(12) United States Patent
Jonsson et al.

(10) Patent No.: US 11,738,317 B2
(45) Date of Patent: Aug. 29, 2023

(54) REACTOR FOR SYNTHESIZING METHANOL OR OTHER PRODUCTS

(71) Applicant: CRI, HF, Kopavogur (IS)

(72) Inventors: Ingi Mar Jonsson, Hafnarfjordur (IS);
Emeric Sarron, Kopavogur (IS);
Asgeir Ivarsson, Kopavogur (IS)

(73) Assignee: CRI, HF, Kopavogur (IS)

( * ) Notice: Subject to any disclaimer, the term of this patent is extended or adjusted under 35 U.S.C. 154(b) by 0 days.

(21) Appl. No.: 17/574,992

(22) Filed: Jan. 13, 2022

(65) Prior Publication Data

US 2022/0226795 A1    Jul. 21, 2022

Related U.S. Application Data

(60) Provisional application No. 63/138,022, filed on Jan. 15, 2021.

(51) Int. Cl.
*B01J 8/02* (2006.01)
*B01J 8/06* (2006.01)
*C07C 29/152* (2006.01)

(52) U.S. Cl.
CPC ............. *B01J 8/0285* (2013.01); *B01J 8/025* (2013.01); *B01J 8/0278* (2013.01); *B01J 8/0292* (2013.01); *B01J 8/065* (2013.01); *C07C 29/152* (2013.01); *B01J 2208/00061* (2013.01); *B01J 2208/00106* (2013.01); *B01J 2208/00336* (2013.01); *B01J 2208/06* (2013.01)

(58) Field of Classification Search
CPC ........ B01J 8/0242; B01J 8/025; B01J 8/0278; B01J 8/0285; B01J 8/0292; B01J 8/065; B01J 2208/00061; B01J 2208/00132; B01J 2208/00336
See application file for complete search history.

(56) References Cited

U.S. PATENT DOCUMENTS

| | | | |
|---|---|---|---|
| 2,549,290 | A | 4/1951 | Congdon et al. |
| 2,727,367 | A | 12/1955 | McKinney |

(Continued)

FOREIGN PATENT DOCUMENTS

| | | | |
|---|---|---|---|
| BR | PI1009035 | B1 | 6/2018 |
| BR | 112013016484 | B1 | 9/2020 |

(Continued)

OTHER PUBLICATIONS

Schliesinger et al., "Fisher-Tropsch Synthesis in Slurry Phase," Engineering and Process Development, vol. 13, Issue No. 6, Jan. 1, 1951, pp. 1474-1479.

(Continued)

*Primary Examiner* — Lessanework Seifu
(74) *Attorney, Agent, or Firm* — WORKMAN NYDEGGER

(57) ABSTRACT

An improved reactor comprising a shell and at least one reactor internal component. The reactor internal component includes a tube bundle comprising a plurality of tubes attached by at least one tube support plate comprising at least one radial strut and at least one bracket configured to secure to at least one tube of the tube bundle. The tubes are arranged in concentric bands about a longitudinal axis of the reactor. The reactor comprises a gas inlet plate, a catalyst support plate, and a top plate.

20 Claims, 15 Drawing Sheets

(56) References Cited

U.S. PATENT DOCUMENTS

| | | | |
|---|---|---|---|
| 3,459,511 A * | 8/1969 | Jotoku et al. | B01J 8/0285 165/174 |
| 3,466,152 A | 9/1969 | Yamamoto et al. | |
| 3,872,025 A | 3/1975 | Singleton | |
| 3,918,934 A | 11/1975 | Kriebel et al. | |
| 3,979,183 A | 9/1976 | Scott | |
| 4,059,076 A | 11/1977 | Kosaka et al. | |
| 4,087,259 A | 5/1978 | Fujitani et al. | |
| 4,249,907 A | 2/1981 | Callejas | |
| 4,272,823 A | 6/1981 | Pool | |
| 4,312,741 A * | 1/1982 | Jacquin | C10G 45/18 208/143 |
| 4,321,234 A * | 3/1982 | Ohsaki | B01J 8/0285 422/205 |
| 4,341,737 A | 7/1982 | Albano et al. | |
| 4,372,755 A | 2/1983 | Tolman et al. | |
| 4,418,236 A | 11/1983 | Cornelius et al. | |
| 4,428,799 A | 1/1984 | Standiford | |
| 4,626,552 A | 12/1986 | Arcuri | |
| 4,717,409 A | 1/1988 | Atkinson | |
| 4,788,369 A | 11/1988 | Marsh et al. | |
| 4,844,837 A | 7/1989 | Heck et al. | |
| 4,910,227 A | 3/1990 | Brown et al. | |
| 5,190,731 A * | 3/1993 | Stahl | F28D 7/16 422/239 |
| 5,342,702 A | 8/1994 | MacGregor | |
| 5,346,593 A | 9/1994 | Cialkowski et al. | |
| 5,416,245 A | 5/1995 | MacGregor | |
| 5,500,449 A | 3/1996 | Benham et al. | |
| 5,602,289 A | 2/1997 | Van Dijk | |
| 5,648,582 A | 7/1997 | Schmidt et al. | |
| 5,715,706 A | 2/1998 | Rathbone | |
| 5,974,826 A | 11/1999 | Baldwin | |
| 6,237,284 B1 | 5/2001 | Erickson | |
| 6,254,807 B1 | 7/2001 | Schmidt et al. | |
| 6,265,453 B1 | 7/2001 | Kennedy | |
| 6,306,917 B1 | 10/2001 | Bohn et al. | |
| 6,736,955 B2 | 5/2004 | Shaw | |
| 6,926,873 B1 | 8/2005 | Filippi et al. | |
| 6,958,135 B1 | 10/2005 | Filippi et al. | |
| 7,144,923 B2 | 12/2006 | Fitzpatrick | |
| 7,347,978 B2 | 3/2008 | Lomax, Jr. et al. | |
| 7,470,811 B2 | 12/2008 | Thiebaut | |
| 7,479,468 B2 | 1/2009 | Van Egmond et al. | |
| 7,968,610 B2 | 6/2011 | Tasso et al. | |
| 8,001,332 B2 | 8/2011 | Bell | |
| 8,198,338 B2 | 6/2012 | Shulenberger et al. | |
| 8,414,840 B2 | 4/2013 | Filippi et al. | |
| 8,506,910 B2 | 8/2013 | Singh et al. | |
| 8,552,074 B2 | 10/2013 | Fu | |
| 8,669,295 B2 | 3/2014 | Fu | |
| 8,729,141 B2 | 5/2014 | Bae et al. | |
| 9,283,531 B2 | 3/2016 | Banerjee et al. | |
| 9,343,764 B2 | 5/2016 | Berlowitz et al. | |
| 9,944,868 B2 | 4/2018 | Bradin | |
| 10,016,699 B2 | 7/2018 | Wakabayashi et al. | |
| 10,196,574 B2 | 2/2019 | Bergins et al. | |
| 10,890,120 B2 | 1/2021 | Hehle et al. | |
| 10,960,349 B2 | 3/2021 | Sarron et al. | |
| 11,192,834 B2 | 12/2021 | Housmans | |
| 11,274,321 B2 | 3/2022 | Reed et al. | |
| 11,292,717 B2 | 4/2022 | Vicari et al. | |
| 11,369,932 B2 | 6/2022 | Sarron | |
| 11,565,982 B2 | 1/2023 | Schuetzle et al. | |
| 11,565,984 B2 | 1/2023 | Hashimoto | |
| 11,572,512 B2 | 2/2023 | Greager et al. | |
| 2002/0113228 A1 | 8/2002 | Kim et al. | |
| 2002/0120017 A1 | 8/2002 | Bohn et al. | |
| 2004/0216465 A1 | 11/2004 | Sheppard et al. | |
| 2004/0265158 A1 | 12/2004 | Boyapati et al. | |
| 2006/0060509 A1* | 3/2006 | Miyauchi | B01J 35/10 208/210 |
| 2006/0211777 A1 | 9/2006 | Severinsky | |
| 2007/0049769 A1 | 3/2007 | Sugiyama et al. | |
| 2007/0244208 A1 | 10/2007 | Shulenberger et al. | |
| 2007/0280862 A1 | 12/2007 | Davis et al. | |
| 2008/0072496 A1 | 3/2008 | Yogev et al. | |
| 2008/0081998 A1 | 4/2008 | Pan et al. | |
| 2008/0084457 A1 | 4/2008 | Hibi et al. | |
| 2008/0084463 A1 | 4/2008 | Kawase | |
| 2008/0115415 A1 | 5/2008 | Agrawal et al. | |
| 2008/0303348 A1 | 12/2008 | Witters | |
| 2008/0319093 A1 | 12/2008 | Olah et al. | |
| 2009/0077866 A1 | 3/2009 | Kalnes et al. | |
| 2009/0163748 A1 | 6/2009 | Bank et al. | |
| 2009/0188867 A1 | 7/2009 | Vuong et al. | |
| 2010/0280135 A1 | 11/2010 | Doty | |
| 2011/0209407 A1 | 9/2011 | Arya et al. | |
| 2012/0148456 A1 | 6/2012 | Filippi et al. | |
| 2015/0075062 A1 | 3/2015 | Bell et al. | |
| 2015/0202547 A1 | 7/2015 | Wakabayashi et al. | |
| 2017/0320796 A1 | 11/2017 | Lee et al. | |
| 2018/0119023 A1 | 5/2018 | Eizenga et al. | |
| 2019/0009237 A1 | 1/2019 | Rizzi | |
| 2022/0306467 A1 | 9/2022 | Mortensen et al. | |

FOREIGN PATENT DOCUMENTS

| | | |
|---|---|---|
| BR | 112015030837 B1 | 8/2021 |
| BR | 112015005715 B1 | 9/2021 |
| BR | 112016004743 B1 | 2/2022 |
| CA | 2354927 A1 | 2/2002 |
| CN | 102497923 B | 6/2012 |
| CN | 102719289 A | 10/2012 |
| CN | 104031710 A | 9/2014 |
| CN | 205803360 U | 12/2016 |
| CN | 107921396 A | 4/2018 |
| CN | 109012508 A | 12/2018 |
| CN | 109294645 A | 2/2019 |
| CN | 217459345 U | 9/2022 |
| DE | 19522083 A1 | 10/1996 |
| DE | 20320020 U1 | 5/2004 |
| DE | 102017010788 A1 | 5/2019 |
| EP | 0135357 A2 | 3/1985 |
| EP | 1569745 A1 | 9/2005 |
| EP | 2450100 A1 | 5/2012 |
| EP | 2831025 B1 | 2/2015 |
| FR | 2583988 A1 | 1/1987 |
| GB | 2158435 A | 11/1985 |
| GB | 2560784 A | 9/2018 |
| IN | 347587 B | 8/2015 |
| IN | 201508083 P1 | 7/2016 |
| IN | 201647012104 A | 7/2016 |
| IN | 201617025179 A | 8/2016 |
| IS | 2300 B | 10/2007 |
| JP | S57126434 A | 8/1982 |
| JP | H03200734 A | 9/1991 |
| KR | 20150086198 A | 7/2015 |
| WO | 0017946 A2 | 3/2000 |
| WO | 03003559 A1 | 1/2003 |
| WO | 2007108014 A1 | 9/2007 |
| WO | 2009021736 A1 | 2/2009 |
| WO | 2009139835 A1 | 11/2009 |
| WO | 2012063034 A2 | 5/2012 |
| WO | 2012092644 A1 | 7/2012 |
| WO | 2013144041 A1 | 10/2013 |
| WO | 2014145082 A2 | 9/2014 |
| WO | 2015042055 A1 | 3/2015 |
| WO | 2017153304 A1 | 9/2017 |
| WO | 2018024764 A1 | 2/2018 |
| WO | 2018107170 A1 | 6/2018 |
| WO | 2020205403 A1 | 10/2020 |

OTHER PUBLICATIONS

Inui et al., "Effective Conversion of Carbon Dioxide to Gasoline," Energy Convers Mgmt, vol. 33, No. 5-8, May-Aug. 1992, pp. 513-520.

Al Fadli, A.M., et al. "Simulation of Transients in a Multi Bed Adiabatic Methanol Synthesis Reactor" Published in the Fourth Saudi Engineering Conference, vol. 5, Nov. 30, 1995, pp. 121-12.

(56) References Cited

OTHER PUBLICATIONS

Shahrokhi, M., et al. "Modeling, Simulation and Control of a Methanol Synthesis Fixed-Bed Reactor," Published in Chemical Engineering Science vol. 60, pp. 4275-4286, Apr. 18, 2005.

Schaschke, "Dictionary of Chemical Engineering", Oxford University Press. Retrieved from hhttps://app.knovel.com/hotlink/pdf/id;kt00TW6WYC/dictionary-chemical-engineering/specific. At least as early as Dec. 31, 2014.

Pérez-Fortes et al., "Methanol Synthesis Using Captured CO2 as Raw Material: Techno-Economic and Environmental Assessment", Applied Energy, vol. 161, Aug. 12, 2015, 15 pages.

Kazemi et al., "Evaluation of Different Vapor Recompression Distillation Configurations Based on Energy Requirements and Associated Costs," Applied Thermal Engineering, vol. 94, 2016, pp. 305-313.

Al-Kalbani et al.,"Comparative Energetic Assessment of Methanol Production from CO2: Chemical Versus Electrochemical Process", Applied Energy vol. 165, Dec. 28, 2015, 13 pages.

Bremer, Jens, et al. "CO2 Methanation: Optimal Start-Up Control of a Fixed-Bed Reactor for Power-To-Gas Applications" Published in Process Systems Engineering, Sep. 2, 2016, 22 pages.

Xu et al., "Process Analysis of Methanol Distillation," Beijing Aerospace Wanyuan Coal Chemical Engineering Technology Co., Ltd., vol. 39, No. 11, 15 Pages.

International Search Report from Corresponding PCT Application No. PCT/IB2022/050268, dated Apr. 7, 2022.

Bukhtiyarova et al., Methanol synthesis from Industrial C02 Sources: A Contribution to Chemical Energy Conversion, Catalysis Letters, Jan. 16, 2017, pp. 416-427, vol. 147.

China Coal Chemical Industry, National Deep Chemical Industry Network, Oct. 11, 2022, retrieved from www.coalchem.org.cn.

Peplow, The Race to Recycle Carbon Dioxide, Nature, Mar. 31, 2022, vol. 603.

Tyhssen Krupp, The Revolution of Green Methanol, as early as Jan. 1, 2022, retrieved from https://www.thyssenkrupp.com/en/stories/sustainability-and-climate-protection/the-revolution-of-green-methanol on Apr. 13, 2023.

* cited by examiner

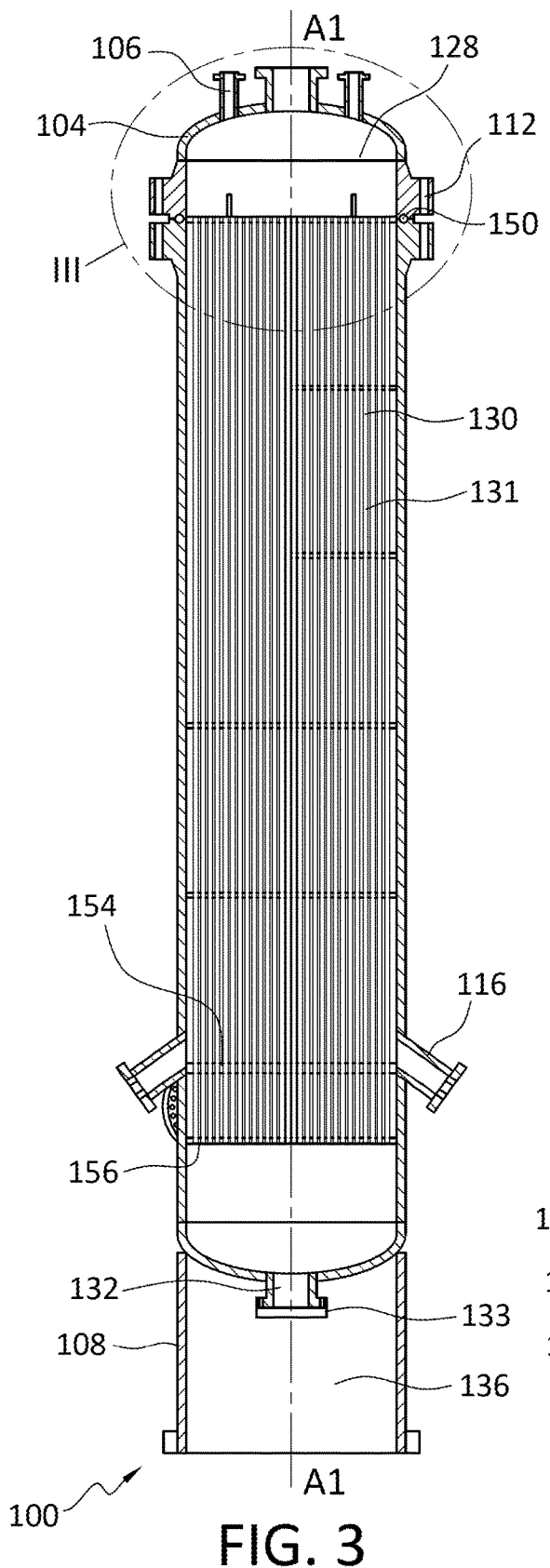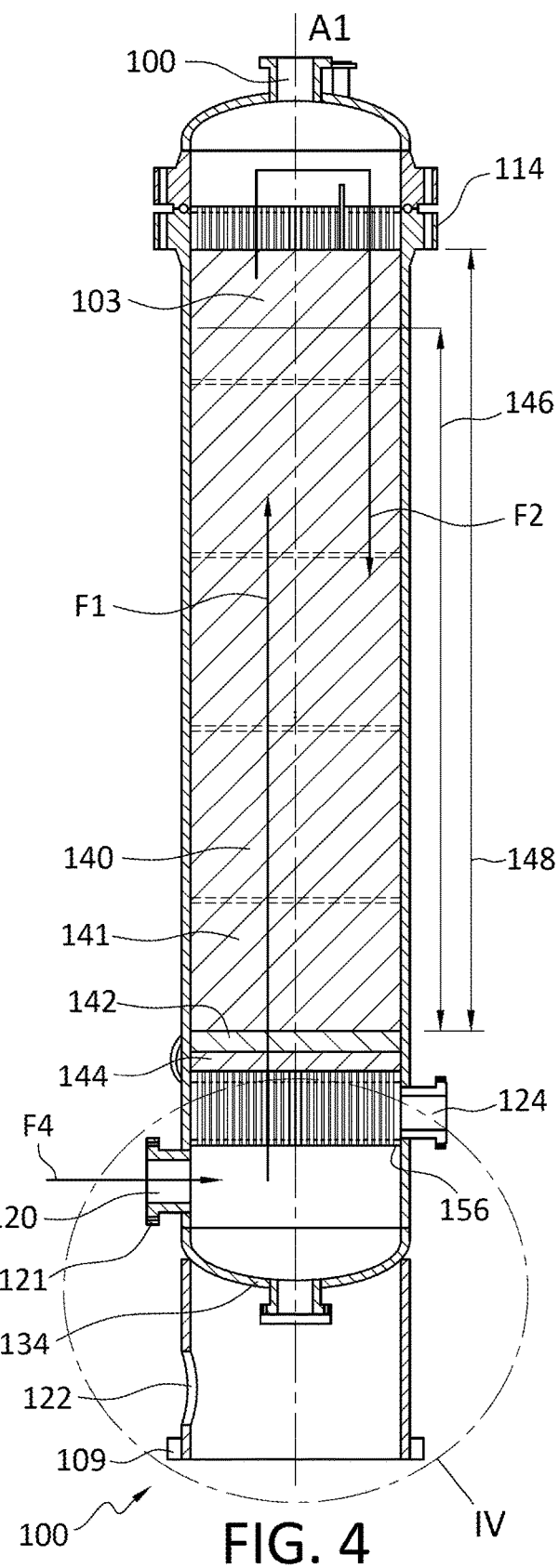
FIG. 3
FIG. 4

REACTOR FOR SYNTHESIZING METHANOL OR OTHER PRODUCTS

CROSS REFERENCE TO RELATED APPLICATION(S)

This application claims the benefit of priority under 35 U.S.C 119(e) to U.S. Provisional Application No. 63/138,022, filed Jan. 15, 2021, the entire contents of which are incorporated herein by reference.

FIELD OF THE DISCLOSURE

The disclosure relates to a reactor, in particular to a reactor for methanol synthesis.

BACKGROUND

Global climate change has been deemed to be the "most pressing environmental challenge of our time." The National Aeronautics and Space Administration (NASA) cites that "scientific evidence for warming of the climate system is unequivocal." Climate change results from the warming effects of greenhouse gases such as water vapor, nitrous oxide, methane, and carbon dioxide. Of these, carbon dioxide emissions are a key culprit, as global atmospheric concentration of $CO_2$ has increased by a third since the Industrial Revolution began. $CO_2$ emissions largely stem from human activities, such as the consumption of fossil fuels, the byproducts of which are emitted into the atmosphere.

Chemical energy storage has been explored as a solution to the problem of renewable energy sources such as wind and solar power being inherently intermittent and unpredictable. Because of the intermittency of wind and solar power, power grids and utilities must meet baseline power demands through fossil fuel-based sources, with suddenly available wind and solar power being difficult to incorporate into the grid due to the difficulty of quickly scaling down and scaling up such fossil fuel-based sources, like coal-fired power plants. Because many renewable energy sources are difficult to scale up as a replacement for traditional fossil fuel-based power sources, high-density energy storage of renewable energy, such that the renewable energy can be stored and used when the grid is able to accommodate the energy, is critical for combating climate change.

Existing energy storage modalities, including thermal energy storage, compressed air energy storage, hydrogen storage, pumped hydroelectric storage, and large-scale batteries have so far proven to be prohibitively expensive and/or difficult to scale up. Chemical storage of renewable energy in the form of electrolyzing water to produce hydrogen, such as for combustion, fuel cell consumption, or chemical synthesis such as methanol synthesis, is a promising approach to providing sufficiently dense and stable storage of renewable energy that may be used when needed, allowing renewable energy to supply energy needs consistently rather than intermittently.

Reactors used in methanol synthesis from syngas are typically limited to boiling water reactors (BWRs) due to the high heat profile of typical reaction suites, which include substantial amounts of CO. BWRs are complex and expensive equipment, but are typically necessary in order to mitigate the heat generated from the exothermic production of methanol from syngas in order to protect the reaction product, the reactor, and the catalyst.

Shell-and-tube reactors for catalytic and/or exothermic reactions, such as synthesizing methanol from $CO_2$ and $H_2$ using a suitable catalyst such as a copper and zinc oxide (Cu/ZnO)-based catalyst or other suitable catalyst, must receive regular maintenance, such as loading and/or removing and recharging catalyst, de-fouling the reactor shell, performing repairs of various components, or otherwise. The ability to access the interior of the reactor for loading catalyst, performing maintenance, and other purposes must be balanced against the need to retain the tubes in a bundle.

Existing designs of shell-and-tube reactors are difficult to scale up or scale down based on the needs of a particular facility, such as a desired throughput. The throughput of the facility may change with time due to debottlenecking efforts, which may increase the throughput requirements of the reactor. Scaling up a reactor for debottlenecking a facility can be a difficult, expensive, and time-consuming endeavor, with the entire reactor, including the internals, needing to be revamped or redesigned in many instances.

This can require significant design and engineering effort, as an engineer must essentially "reinvent the wheel" when scaling up the design, with consideration given to the arrangement and cross-sectional area of the tubes, the size and configuration of the shell, the volume and cross-sectional surface area of the catalyst bed, among other things. Existing shell-and-tube reactor designs and providers are poorly suited to adapting reactor designs to changing requirements in an efficient manner. If the reactor is not properly designed, uneven distribution of catalyst, reactants, and heat may result, which can damage the catalyst and/or components of the reactor and reduce the efficiency of the reaction. In some cases, a runaway exothermic reaction can result in catastrophic failure of the reactor.

Additionally, it is difficult to scale and properly fabricate feed tubes in and/or for a reactor. Improperly designed, arranged, and/or fabricated feed tubes often lead to the creation of blockages, eddies, and uneven areas of reactants within reactors, which disadvantageously reduces the efficiency and throughput of a reactor and can result in hot spots. Hot spots in exothermic reactions are particularly dangerous and damaging to the reactor and catalyst.

Another problem in reactor design is the difficulty of measuring internal reactor temperature at one or more desired locations. It is difficult to properly control a process including a reactor, particularly in high-risk applications such as exothermic reactions, without an understanding of the temperature profile of the reactor internals, particularly at different locations along the reactor body corresponding to different stages of the reaction and/or different reactor conditions.

However, thermocouple joints including a gasket seat may sustain damage over time, leading to thermocouple joint leakage. While such leakages may be repaired, doing so requires deactivating the catalyst and replacing the gasket seat. This involves costly, potentially dangerous, and time-consuming shut-downs, deactivation of catalyst, and start-ups, each of which entails high costs, including substantial opportunity costs. Given that the expected lifetime of catalysts tends to be between three and five years, such repairs constitute highly expensive disruptions to the operation of a facility. Further, in high pressure and/or temperature reactions involving hydrogen, the risk of leakage from flanged joints is particularly high, both of hydrogen or other reactants/products outwardly and of oxygen, a catalyst poison, inwardly.

Accordingly, existing reactor designs that incorporate multiple thermowells for providing thermocouples at different elevational locations along a reactor body are susceptible to significant operational disruptions due to thermocouple joint leakage, and reactor designs that omit such thermowells to avoid disruptions lack the necessary reactor-conditions data to properly control the reaction. Additionally, existing thermowell configurations in reactors insert the thermocouple transversely to a flow direction, e.g. radially into the reactor body. This disadvantageously results in temperature readings for larger reactors of conditions close to the outer shell, which further renders scaling of a reactor design difficult. Reactor designs are further ill-suited to allowing a thermocouple to be inserted into the reactor body when the catalyst is present without damaging the thermocouple.

Existing reactor designs may comprise one or more nozzles for unloading spent catalyst, for example from a bottom portion of the reactor body. The configuration of existing reactors' catalyst-unloading nozzles is poorly adapted to effectively and quickly removing catalyst, such that an operator must scrape catalyst out of the reactor body.

Certain shell-and-tube-type reactors and other types of reactors may comprise an inlet nozzle from which reactant gases are routed through a pipe extending through a center of the reactor body. The pipe may be drilled to fit one or more feed tubes, which each may be bent to both connect to the pipe and then feed the reactant upwardly through the reactor body. Such reactor configurations are not adapted to scaling up, for example to several hundred tubes, given the precise and tube-specific adjustments that must be made to connect the pipe to each of the feed tubes.

The inlet pipe in certain reactor configurations is further utilized to support the feed tubes at different elevations within the reactor body, with one or more flat bars welded to and extending between the inlet pipe and one or more feed tubes. This configuration is highly time-consuming particularly for manufacturing, assembling, and maintaining a large-scale reactor, which complicates the task of scaling a reactor design depending on the requirements of a facility. Additionally, the inlet pipe disadvantageously occupies significant cross-sectional area that could otherwise be occupied by catalyst. While tie rods have been contemplated for supporting feed tubes in shell-and-tube reactors, such supports take up catalyst space and present obstructions during catalyst loading and unloading.

From the foregoing, there is a need for an improved reactor that is configured for maintaining the reactor internals and managing the catalyst, for scaling the reactor throughput up or down based on the throughput needs of a facility, for improved measurement of reactor conditions without compromising reactor integrity and maintainability, for effectively removing spent catalyst, for improved manufacture, and for overcoming the challenges of constructing a shell-and-tube reactor.

SUMMARY

Reactor embodiments according to the present disclosure advantageously address the drawbacks of existing reactor designs by providing a reactor that is scalable and/or configured for improved access and maintainability of the reactor, particularly of an interior of the reactor. The reactor embodiments may be configured to facilitate access to the reactor internals without sacrificing strength and robustness of the reactor internals, such as a reactor tube bundle comprising one or more tubes and one or more support structures, such that the tube bundle remains intact and undamaged.

The reactor embodiments further comprise a tube arrangement that is configured for scaling up or down readily based on the needs of a particular facility. Whereas in existing reactor designs, tubes cannot be easily added to or removed from a tube bundle in accordance with a reactor shell shape when building a reactor without significant redesign work, the embodiments of the present disclosure advantageously allow for circumferential bands or other arrangements of tubes to be modularly arranged based on the required throughput of the reactor and the associated facility. In embodiments the arrangements of tubes may define regular and/or repeating patterns that can be simply added to and/or removed from an existing tube bundle design when designing a reactor. This has the advantage of making debottlenecking operations or other design work much easier and less costly from a manufacturing perspective.

The arrangement of the tube bundle further facilitates heat and reactant distribution throughout the reactor interior, in particular through the catalyst bed, without disrupting catalyst loading, which typically occurs as an operator loads or dumps the catalyst particles into the reactor interior from an open top end of the reactor. The arrangement of the reactor and the tube bundle of embodiments advantageously provides both modularity of design for improved constructability while maintaining desired properties regarding heat and reactant distribution while also ensuring that the catalyst particles are evenly distributed within the reactor interior.

The tube bundle of reactor embodiments according to the disclosure are further configured to provide improved structural support to one or more tubes for increased robustness of the reactor during construction, transportation, and installation, as well as during operation. In embodiments, one or more structural supports are provided and/or one or more of the tubes is provided with increased thickness for ensuring structural support at desired locations of the tube bundle.

In embodiments, the reactor and components thereof are configured to facilitate easy access for maintenance of critical parts. One or more plates configured for supporting the tube bundle may be modular such that an operator may load catalyst, unload catalyst, or access components in the reactor interior with ease compared to existing reactors, where components such as support plates are welded to an interior surface of the reactor shell and prohibit access to the reactor internal components.

The reactor embodiments address the problem of existing reactor designs being poorly suited to provide proper flow and reactant distribution, and consequently heat distribution, within the reactor and the catalyst bed, by providing an improved inlet nozzle and distribution mechanism configured to directing reactants into a tube bundle arranged within an interior of the reactor. In embodiments, the inlet nozzle is provided proximate a gas inlet plate and is arranged with a flow direction transverse to a flow direction of the tubes of the tube bundle. A secondary inlet nozzle may be provided at a bottom of the reactor and may be configured with a structure for evenly distributing flow into the tubes of the tube bundle. In embodiments, one or more catalyst unloading nozzles are provided in an improved configuration for removing catalyst, with the unloading nozzles configured at a downward angle.

The tube bundle and the tubes may be arranged such that a cross-sectional area of the tubes relative to a cross-sectional area of the catalyst is improved for even heat and flow distribution without interfering with the structural and modularity features of the tube bundle.

The reactor embodiments are further configured to reduce the incidence of blockages, eddies, and/or uneven areas of reactants within the reactor body and accompanying hot spots by providing for an improved distribution of catalyst, reactor internals, and reactants during the course of a reaction.

The reactor embodiments of the present disclosure further address the disadvantages of existing reactor designs regarding process control and temperature measurement. In embodiments, the reactor is configured to provide one or more thermowells configured to receive one or more respective thermocouples. The thermocouples may be configured to measure a temperature of the reactor interior at a plurality of locations using respectively a single thermowell arranged axially or longitudinally relative to the reactor body.

An example embodiment according to the present disclosure may be directed to a reactor, comprising: a shell defining an internal space; at least one inlet nozzle; and a tube bundle comprising one or more tubes.

An embodiment may further comprise a catalyst support plate.

An embodiment may further comprise at least one tube support plate.

An embodiment may further comprise a gas inlet plate.

An embodiment may further comprise a top plate.

An embodiment may further comprise a top plate and tube support plate.

An embodiment may further be configured where the shell is configured to receive at least one catalyst.

In an embodiment, the at least one catalyst is a solid catalyst. Such catalyst may comprise balls of a first diameter.

In an embodiment the solid catalyst comprises balls of a second diameter.

In embodiment the shell is configured to receive at least one solid catalyst. Such solid catalyst may comprise a shape defining at least one of pellets, rings, tablets, or spheres.

In an embodiment, the catalyst support plate is configured to support a height of the solid catalyst.

In an embodiment, the catalyst support plate defines one or more apertures.

In an embodiment, the one or more apertures comprise a plurality of apertures of a first size and a plurality of apertures of a second size, the apertures extending through at least part of a thickness of the catalyst support plate.

In an embodiment, the first size corresponds to a circumference of at least one tube of the tube bundle.

In an embodiment, the second size is smaller than the first size.

In an embodiment, the second size is a function of the thickness of the catalyst support plate.

In an embodiment, the apertures of the first size are defined through the catalyst support plate according to an arrangement of the plurality of tubes.

In an embodiment, the gas inlet plate comprises a plurality of apertures defined through a thickness of the gas inlet plate.

In an embodiment, the plurality of apertures are circular apertures defined through the gas inlet plate according to the arrangement of the plurality of tubes.

In an embodiment, the gas inlet plate further comprises a second plurality of apertures defined through the thickness of the gas inlet plate, the second plurality of apertures comprising a different size and/or shape than the plurality of circular apertures.

In an embodiment, the shell defines an outlet nozzle.

In an embodiment, the outlet nozzle is located at a side portion of the shell.

In an embodiment, the inlet nozzle is located proximate a bottom portion of the shell.

In an embodiment, the inlet nozzle is arranged transverse to a direction of flow through the shell.

In an embodiment, the inlet nozzle is arranged substantially parallel to a direction of flow through the shell.

In an embodiment, the gas inlet plate is arranged proximate the inlet nozzle.

In an embodiment, the at least one tube support plate comprises at least one circumferential band.

In an embodiment, the at least one circumferential band comprises at least one bracket configured to extend about a portion of a tube of the tube bundle.

In an embodiment, the at least one bracket extends about an entirety of the tube.

In an embodiment, the shell defines a startup nozzle configured for the provision of a heating fluid.

In an embodiment, the reactor further comprises at least one catalyst unloading nozzle.

In an embodiment, the reactor further comprises a hand hole.

In an embodiment, the at least one tube support plate defines a plurality of concentric circumferential bands.

In an embodiment, the tube bundle comprises at least one tube of a first size and at least one tube of a second size.

In an embodiment, the inlet nozzle is arranged below the gas inlet plate.

In an embodiment, the shell defines an outlet nozzle, and wherein the outlet nozzle is arranged below the catalyst support plate.

In an embodiment, catalyst (e.g., balls) of the first size (e.g., diameter) and the catalyst (e.g., balls) of the second size (e.g., diameter) are arranged in discrete, respective layers proximate the catalyst support plate.

In an embodiment, the shell is configured to receive at least one solid catalyst, wherein the catalyst defines a first height within the shell in an unreduced state and a second height within the shell in a reduced state (e.g., due to settling that may occur during operation).

In an embodiment, the second height is lower than the first height.

In an embodiment, the at least one tube support plate defines at least one radial strut connected to at least one of the plurality of circumferential bands.

In an embodiment, the at least one radial strut connects to at least one of the circumferential bands and to an outer support band.

In an embodiment, an innermost circumferential band of the at least one tube support plate comprises a number of brackets (e.g., six) configured respectively to correspond to a ring of the same number of innermost tubes of a first size.

In an embodiment, a second circumferential band of the at least one tube support plate comprises an equal or greater number of brackets than the previous band (e.g., 10) configured respectively to correspond to a concentric band (e.g., ring) of the same number of tubes of the tube bundle located in the second concentric band or ring of tubes. Such tubes may be of the first size.

In an embodiment, a third circumferential band of the at least one tube support plate comprises an equal or greater number of brackets than the previous band (e.g., 14) configured respectively to correspond to a concentric band (e.g., ring) of the same number of tubes of the tube bundle located in the third concentric band or ring of tubes. Such tubes may be of the second size.

In an embodiment, a fourth circumferential band of the at least one tube support plate comprises an equal or greater number of brackets than the previous band (e.g., 18) configured respectively to correspond to a concentric band (e.g., ring) of the same number of tubes of the tube bundle located in the fourth concentric band or ring of tubes. Such tubes may be of the first size.

In an embodiment, a fifth circumferential band of the at least one tube support plate comprises an equal or greater number of brackets than the previous band (e.g., 22) configured respectively to correspond to a concentric band (e.g., ring) of the same number of tubes of the tube bundle located in the fifth concentric band or ring of tubes. Such tubes may be of the first size.

In an embodiment, a sixth circumferential band of the at least one tube support plate comprises an equal or greater number of brackets than the previous band (e.g., 26) configured respectively to correspond to a concentric band (e.g., ring) of the same number of tubes of the tube bundle located in the sixth concentric band or ring of tubes. Such tubes may be of the first size.

In an embodiment, a seventh circumferential band of the at least one tube support plate comprises an equal or greater number of brackets than the previous band (e.g., 30) brackets configured respectively to correspond to a concentric band (e.g., ring) of the same number of tubes of the tube bundle located in the seventh concentric band or ring of tubes. Such tubes may be of the second size.

In an embodiment, an eighth circumferential band of the at least one tube support plate comprises an equal or greater number of brackets than the previous band (e.g., 34) configured respectively to correspond to a concentric band (e.g., ring) of the same number of tubes of the tube bundle located in the eighth concentric band or ring of tubes. Such tubes may be of the first size.

In an embodiment, a ninth circumferential band of the at least one tube support plate comprises an equal or greater number of brackets than the previous band (e.g., 36) configured respectively to correspond to a concentric band (e.g., ring) of the same number of tubes of the tube bundle located in the ninth concentric band or ring of tubes. Such tubes may be of the first size.

In an embodiment, a tenth circumferential band of the at least one tube support plate comprises an equal or greater number of brackets than the previous band (e.g., 42) configured respectively to correspond to a concentric band (e.g., ring) of the same number of tubes of the tube bundle located in the tenth concentric band or ring of tubes. Such tubes may be of the first size.

In an embodiment, an eleventh circumferential band of the at least one tube support plate comprises an equal or greater number of brackets than the previous band (e.g., 46) configured respectively to correspond to a concentric band (e.g., ring) of the same number of tubes of the tube bundle located in the eleventh concentric band or ring of tubes. Such tubes may be of the second size.

In an embodiment, a twelfth circumferential band of the at least one tube support plate comprises an equal or greater number of brackets than the previous band (e.g., 50) configured respectively to correspond to a concentric band (e.g., ring) of the same number of tubes of the tube bundle located in the twelfth concentric band or ring of tubes. Such tubes may be of the first size.

In an embodiment, a thirteenth circumferential band of the at least one tube support plate comprises an equal or greater number of brackets than the previous band (e.g., 54) configured respectively to correspond to a concentric band (e.g., ring) of the same number of tubes of the tube bundle located in the thirteenth concentric band or ring of tubes. Such tubes may be of the first size.

In an embodiment, a fourteenth circumferential band of the at least one tube support plate comprises an equal or greater number of brackets than the previous band configured respectively to correspond to a concentric band (e.g., ring) of the same number of tubes of the tube bundle located in the fourteenth concentric band or ring of tubes. Such tubes may be of the second size.

It will be apparent that any number of circumferential bands may be provided.

In an embodiment, any of the circumferential bands of the at least one tube support plate further comprises brackets corresponding to at least one thermocouple insertion tube, the at least one thermocouple insertion tube. Such thermocouple insertion tube may be similarly sized relative to the tubes of the tube bundle (e.g., of the first or second size).

In an embodiment, at least four tube support plates are arranged longitudinally along the tube bundle.

In an embodiment, at least one tube support plate is arranged longitudinally along the tube bundle, wherein a circumferential band of the at least one tube support plate further comprises brackets corresponding to at least one thermocouple insertion tube, wherein the at least one thermocouple insertion tube is configured to receive a temperature measurement device.

In an embodiment, the temperature measurement device is configured to obtain a temperature at a plurality of longitudinal locations within the reactor.

In an embodiment, the temperature measurement device is configured to obtain a temperature at a plurality of locations (e.g., at least eight different locations), e.g., longitudinally along the reactor.

In an embodiment, the shell defines at least one flange facilitating attachment and detachment of an upper portion of the shell from a main body portion of the shell.

In an embodiment, the shell is configured to attach to a skirt at a bottom portion of the shell.

In an embodiment, the skirt defines an aperture configured to receive an inlet spool.

In an embodiment, the at least one tube support plate defines at least one radial strut connected to at least one of a plurality of circumferential bands of the tube support plate, wherein the at least one radial strut of the at least one tube support plate aligns axially with at least one radial strut of another tube support plate.

In an embodiment, the at least one radial strut of the at least one tube support plate is offset axially relative to at least one radial strut of an adjacent tube support plate.

In an embodiment, the at least one tube support plate defines a plurality of radial struts arranged symmetrically about a longitudinal axis of the reactor.

In an embodiment, the at least one tube support plate defines at least one radial strut connected to at least one of a plurality of circumferential bands of the tube support plate, wherein the at least one circumferential band of the at least one tube support plate is removably secured to the at least one radial strut.

In an embodiment, at least one tube of the tube bundle defines a uniform thickness longitudinally within the reactor.

In an embodiment, at least one tube of the tube bundle defines a tapered thickness longitudinally within the reactor.

In an embodiment, at least one tube of the tube bundle is configured to facilitate a greater degree of heat transfer proximate a bottom portion of the reactor relative to a top portion of the reactor.

Any of the features noted above, or other features described herein may be used in combination with one another, alone, or in combination with other features.

Other methods, embodiments, and variations of the system are described in greater detail in the following discussion.

BRIEF DESCRIPTION OF THE DRAWINGS

These and other features, aspects, and advantages of the present invention will become readily apparent and better understood in view of the following description, appended claims, and accompanying drawings.

FIG. 3 is a cutaway elevational view of the reactor and reactor internals of the embodiment of FIG. 1A taken along the line 1A-1A.

FIG. 4 is a cutaway elevational view of the reactor and catalyst bed and catalyst support layers of the embodiment of FIG. 1A taken along the line 1A-1A.

DETAILED DESCRIPTION OF VARIOUS EMBODIMENTS

Figure 1A:
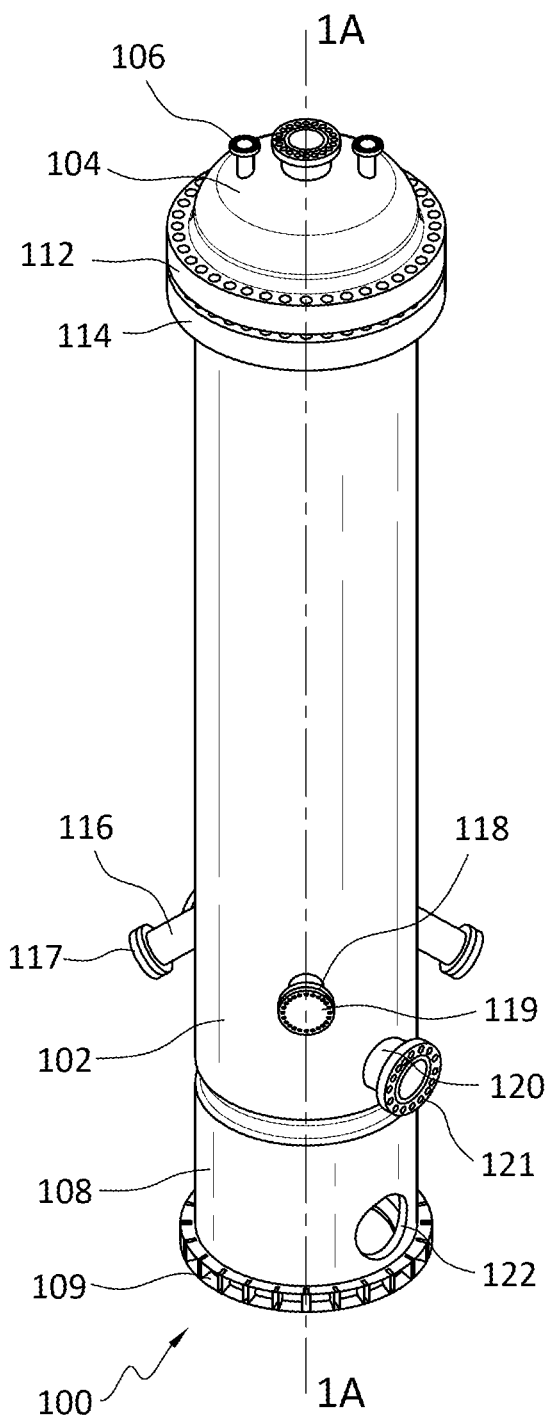
FIG. 1A is a perspective view of a reactor according to an embodiment of the present disclosure.

A better understanding of different embodiments of the invention may be had from the following description read with the accompanying drawings in which like reference characters refer to like elements.

While the disclosure is susceptible to various modifications and alternative constructions, certain illustrative embodiments are shown in the drawings and will be described below. It should be understood, however, there is no intention to limit the disclosure to the embodiments disclosed, but on the contrary, the intention is to cover all modifications, alternative constructions, combinations, and equivalents falling within the spirit and scope of the disclosure and defined by the appended claims.

It will be understood that, unless a term is defined in this patent to possess a described meaning, there is no intent to limit the meaning of such term, either expressly or indirectly, beyond its plain or ordinary meaning.

Turning to FIG. 1A, a reactor 100 according to embodiments of the present disclosure is shown. The reactor 100 comprises a shell 102 defining an internal space 103 (FIG. 4) and comprising at least one inlet nozzle 120. The reactor 100 is configured to receive and cooperate with at least one reactor internal component, such as a tube bundle 130 (FIG. 3) comprising one or more tubes 131. The reactor 100 extends longitudinally about an axis 1A-1A from a top end 105 to a bottom end 107 and may define a substantially cylindrical shape.

The inlet nozzle 120 is arranged generally proximate the bottom end 107 such that one or more reactants may enter through the inlet nozzle 120 and then travel upwardly in a direction F1 (FIG. 4) through the internal space 103 of the reactor 100 within the one or more tubes 131 before exiting the tubes 131 proximate the top end 105 and diverting downward in a direction F2 toward an outlet nozzle 124 which defines a corresponding flange 125. As the reactants travel upwardly through the one or more tubes 131, the reactants exchange heat with the catalyst and the reactants and products traveling downwardly in the direction F2 (FIG. 4).

In exothermic reactions such as methanol synthesis, the reactants advantageously absorb heat generated by the reaction within the tubes 131 to pre-heat the reactants prior to delivering the reactants to a catalyst bed 140. This also advantageously mitigates the formation of catalyst hotspots and associated catalyst sintering and product degradation. This also reduces the likelihood of a runaway reaction, as the reactants define a heat exchange medium for removing heat from the catalyst bed. Due to the distribution of the tubes 131, the reactants form a much more effective heat-exchange modality than, for example, a cooling-water sleeve surrounding the reactor 100.

The reactor 100 may define, in addition to the inlet nozzle 120 and the outlet nozzle 124, one or more catalyst unloading nozzles 116 and/or one or more hand holes 118 through which the internal space 103 is accessible. The one or more catalyst unloading nozzles 116 may be angled downwardly so as to facilitate gravity-based removal of the catalyst from the catalyst bed 140, for example when removing and recharging spent catalyst. The one or more hand holes 118 may facilitate maintenance by allowing a technician to insert a hand, tool, or instrument into the internal space 103 proximate the catalyst support plate 154, the catalyst bed 140, or at any other suitable location.

Figure 1B:
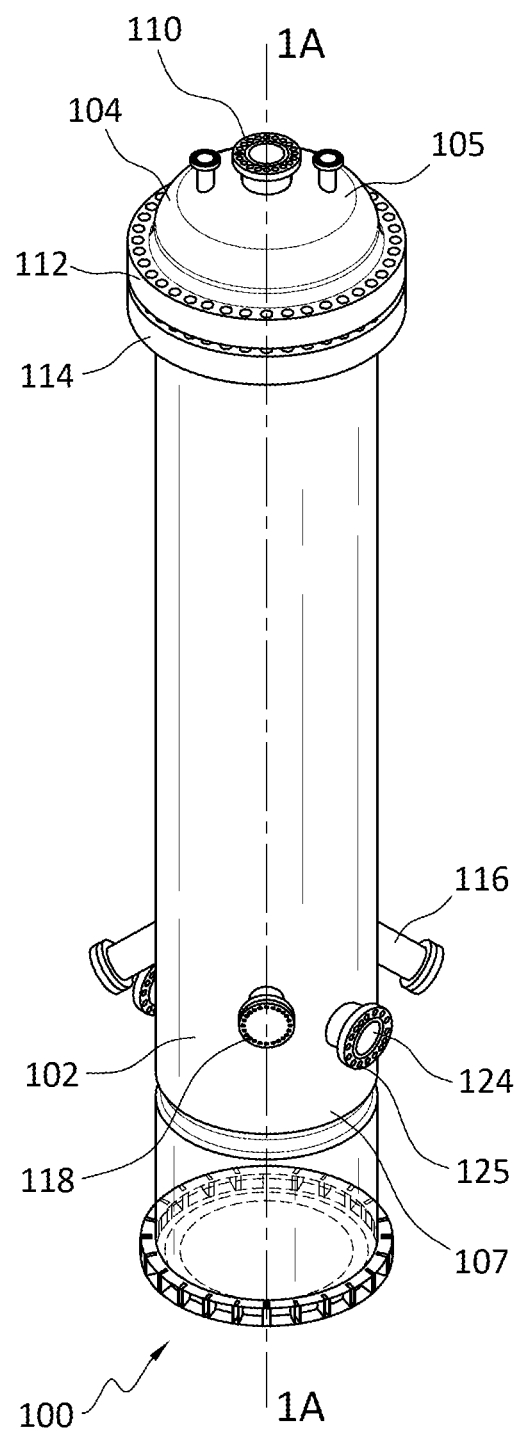
FIG. 1B is a rotated perspective view of the reactor according to the embodiment of FIG. 1A.

As seen in FIGS. 1A and 1B, the reactor 100 defines a startup nozzle 110 configured for the provision of a heating fluid. During a startup operation, when the reaction has not yet reached steady-state operation, the reactants may not receive a necessary amount of pre-heat as they travel in the direction F1 in the tube bundle 130. The startup nozzle 110 may receive a heating fluid such as an inert gas, like heated nitrogen gas, that may pass through the internal space 103 and provides enough enthalpy to achieve steady-state operation without adversely affecting the yield of the reaction.

The shell 102 further may define at least one thermocouple port 106. Each thermocouple port 106 may facilitate the insertion of a temperature measurement device into the reactor 100 and in embodiments into the tube bundle 130 in an axial or longitudinal direction. By positioning the thermocouple port 106 at a top portion 105 of the reactor 100, a single temperature measurement device, such as a thermocouple, may be inserted therethrough with the ability to measure temperature at a plurality of locations. In embodiments, the temperature measurement device may extend in an elongate manner and comprise a plurality of measurement devices such as thermocouples thereon at predetermined distances such that the reactor conditions at each of said predetermined distances may be measured for improved control of the reaction.

While two thermocouple ports 106 are shown in FIGS. 1A and 1B on opposite sides of the startup nozzle 110, it will be appreciated that more or fewer thermocouple ports 106 may be provided at any suitable location. By providing the temperature measurement devices through the thermocouple ports 106, the reactor 100 advantageously allows for measurement of reactor conditions at different elevational locations in the reactor while minimizing the number of thermocouple joints, thereby facilitating improved process control and throughput while minimizing the risk of leaks, either into or out of the shell 102. The location of the thermocouple ports 106 further allows for sampling the reactor conditions at desired radial locations of the reactor 100 regardless of the size of the reactor 100, in contrast to existing reactor designs in which the thermocouples are inserted radially, such that larger reactors are sampled disproportionately close to the shell.

Turning to FIG. 4, the shell 102 may define an inlet nozzle 120 with a corresponding flange 121 arranged a distance below a gas inlet plate 156 and both arranged proximate the bottom end 107 of the reactor 100. The inlet nozzle 120 may be arranged transverse relative to a longitudinal extension direction of the reactor 100, such that as the reactants enter through the inlet nozzle 120 in a flow direction F4, the reactants change direction and enter into one or more tubes 131 of the tube bundle 130 through the gas inlet plate 156 in the direction F1.

The inlet nozzle 120 may be arranged as shown to optimize a distance between the inlet nozzle 120 and a bottom of the tube bundle 130 and to evenly distribute the reactants to the tubes 131 such that eddies that result in blockages, hot spots, and uneven flow are avoided. The flange 121 may be configured to facilitate attachment of a reactant feed line to the nozzle 120. While the inlet nozzle 120 has been shown and described, it will be appreciated that the distance between the inlet nozzle 120 and the bottom of the tube bundle 130 may be greater or smaller as suitable.

Figure 5A:
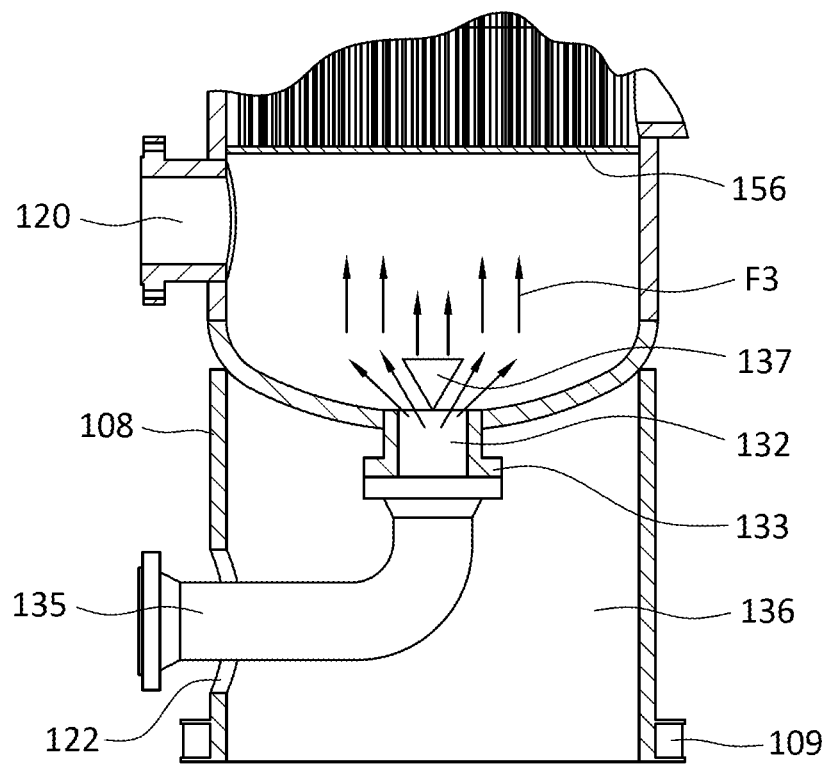
FIG. 5A is a close-up elevational cutaway view of the reactor of the embodiment of FIG. 1A according to the detail IV.

Additionally or as an alternative, the shell 102 further defines a secondary inlet nozzle 132 with a corresponding flange 133 as shown in FIG. 5A. The flange 133 may be configured to facilitate attachment of a reactant feed line to the nozzle 132. The secondary inlet nozzle 132 is arranged to deliver the reactants vertically in a direction F3, which may correspond to or be parallel with the flow direction F1 upwardly through the tubes 131. The reactor shell 102 may be secured with a skirt 108 which may define through a thickness thereof an aperture 122 configured to receive an inlet spool 135 connecting to the secondary inlet nozzle 132.

The skirt 108 may be cylindrical in shape and extend substantially coextensively with the reactor shell 102 downwardly from the bottom end 107. The skirt 108 may define a ring 109 at grade securing the reactor 100 and the skirt 108 in position. The inlet spool 135 may be curved such that the reactants are fed toward the reactor 100 in a flow direction generally transverse to the flow direction F3, for example in a direction substantially parallel to the direction F4 of the inlet nozzle 120. The inlet nozzle 120 and the secondary inlet nozzle 132 may be configured to operate simultaneously or independently of each other. While a skirt has been shown and described, any suitable support may be utilized, and the disclosure is not limited to the use of a skirt.

In embodiments, a diverter 137 may be removably arranged within the secondary inlet nozzle 132 or the shell 102 for directing a flow direction of the reactants when the secondary inlet nozzle 132 is in use. The diverter 137 may define a shape that distributes a portion of the flow of reactants from the secondary inlet nozzle 132 radially outward such that the flow is evenly distributed between the central tubes, which are generally aligned with the secondary inlet nozzle 132, and outer tubes. While the diverter 137 has been shown and described, it will be appreciated that any suitable structure, configuration, or arrangement may be utilized. In embodiments, the diverter 137 defines a plurality of apertures and/or protrusions configured for distributing the flow of the reactants entered through the nozzle 132.

Figure 5B:
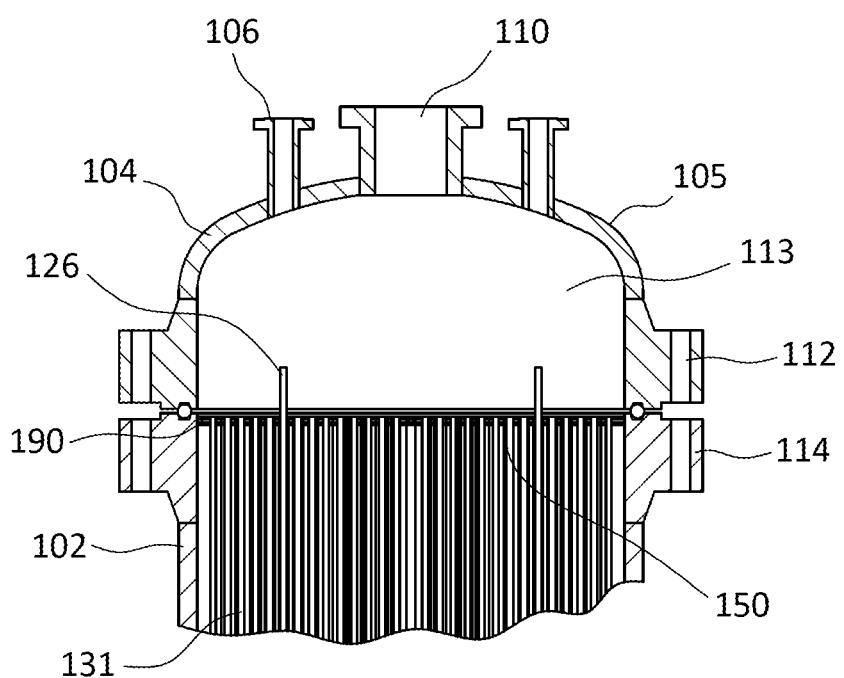
FIG. 5B is a close-up elevational cutaway view of the reactor of the embodiment of FIG. 1A according to the detail III.

Turning to FIG. 5B, the reactor 100 may further comprise a domed head portion 104 that is detachable from the shell 102 and is releasably attached thereto at flanges 112, 114 which may comprise any suitable modality for attaching the domed head portion 104 and the shell 102, such as apertures and corresponding fasteners. The domed head portion 104 may define a space 113 above a top extent of the tube bundle 130. The space 113 provides a space for the pre-heated reactants to mix and divert back downwardly through the catalyst bed 140. The nozzle 110 may be defined through a thickness of the domed head portion 104 to allow for the addition of a heating medium during start-up operation, as described previously.

While a domed head portion releasably securable to a shell has been shown and described, it will be appreciated that the disclosure is not limited thereto, and for any size of reactor, a fixed head, for example comprising a flanged manhole, may be utilized instead.

The thermocouple ports 106 may be aligned with respective thermocouple insertion tubes 126, which may extend a distance above the top extent of the tube bundle 130. The thermocouple ports 106 may extend through a part or an entirety of a thickness of the domed head portion 104 to allow access to the reactor interior 103. The thermocouple ports 106 may facilitate access to the reactor interior 103 in any suitable way, such as by defining an aperture of a size that is configured to be flush with a surface of the temperature measurement device such that pressure may be maintained within the reactor interior 103, by cooperating with a gasket seal, combinations thereof, or any other suitable means. Any suitable modality may be used. By extending a distance above the top extent of the tube bundle 130, the thermocouple insertion tubes 126 are configured to be more easily identified during installation of the thermocouple, particularly as access is limited when the domed head portion 104 is in place. The thermocouple insertion tubes 126 may extend along a length of the reactor 100 substantially parallel to or aligned with the feed tubes 131.

The reactor 100 further may comprise one or more of a catalyst support plate 154, at least one tube support plate 162, 163, 164, 165, a gas inlet plate 156, a top and feed tube support plate 150, and/or a top plate 190, the provision of which advantageously facilitates securing the tube bundle 130 within the shell 102 while allowing for access to the reactor interior 103 as necessary for maintenance or other purposes. The gas inlet plate 156 and the catalyst support plate 154 may advantageously be welded to an interior surface of the shell 102 to secure the tube bundle 130 therewithin.

The tubes 131 of the tube bundle 130 may be welded to the gas inlet plate 156, the top and feed tube support plate 150, and/or to the at least one tube support plate 162, 163, 164, 165. In embodiments, only the gas inlet plate 156 is welded or otherwise secured to the interior surface of the reactor shell 102, with the top and feed tube support plate 150 and the at least one tube support plate 162, 163, 164, 165 being unsecured so as to accommodate thermal expansion of the tubes 131.

Turning to FIG. 4, the catalyst bed 140 may comprise one or more sections of catalyst, such as solid catalyst. The catalyst bed 140 may also or alternatively comprise one or more inert sections 142, 144, which sections may comprise support ceramic balls of a first diameter, such as 1-30 mm, more specifically 5-20 mm, or in embodiments 9 mm. The catalyst bed 140 may also comprise support ceramic balls of a second diameter, such as 1-30 mm, more specifically 10-25 mm, or in embodiments 19 mm. The catalyst bed 140 may define distinct sections 142, 144 corresponding to ceramic balls comprising substantially only balls of a single size.

For example, in the depicted embodiment the section 142 comprises substantially only balls having a diameter of 9 mm while the section 144 comprises only balls having a diameter of 19 mm. The sections 142, 144 may have any suitable height within the reactor 100, such as 5-500 mm, more specifically 100-300 mm, or in embodiments 200 mm for each of the sections 142, 144. The height of sections 142, 144 may the same, or different from one another. The catalyst bed 140 may additionally or alternatively comprise solid catalyst having a shape defining at least one of pellets, rings, tablets, or spheres. The sections 142, 144 may be arranged proximate (e.g., above, or directly above) the catalyst support plate 154 and below a section 141 comprising substantially only solid catalyst of a different shape and/or size than the support ceramic balls of sections 142, 144.

The support ceramic balls sections 142, 144 advantageously support a weight of the catalyst in the catalyst bed while promoting effective and even flow distribution. By providing distinct first and second sections 142, 144, the flow of reactants, products, and byproducts through the reactor interior 103 toward the outlet nozzle 124 is improved as the flow of gases is allowed between the catalyst particles in the catalyst bed 140, between the support ceramic balls of the first, smaller diameter in the first section 142, and finally between the support ceramic balls of the second, larger diameter in the second section 144 prior to passing through the catalyst support plate 154. The support ceramic balls may advantageously be inert and configured to resist thermal shock and corrosion from various reactants, products, and/or byproducts. While support ceramic balls have been described, it will be appreciated that the sections 142, 144 may have more or fewer sections and may comprise differently shaped or sized support structures, such as rings, cylinders, polygons, or otherwise.

In embodiments, the section 141 of the catalyst bed 140 may have or define a first height 148 corresponding to an unreduced catalyst height, and a second height 146 corresponding to a reduced catalyst height.

While the section 141 of the catalyst bed 140 may comprise catalyst particles of a single size and/or shape, it will be appreciated that distinct sections within the catalyst bed 140 of differently sized and/or shaped catalyst particles are contemplated within the scope of the present disclosure. The catalyst particles may have any suitable shape or configuration, such as spheres, pellets, cylinders, trilobes, quadralobes, pyramids, cones, stars, or otherwise, and may have any suitable number and size of apertures defined therethrough and/or notches or grooves defined on a portion of the surface thereof. Distinct sections corresponding to a single, different type of catalyst size and/or shape may be provided in the catalyst bed 140, for example as axial or radial layers or pockets. In embodiments different sizes and shapes of catalyst particles may be provided and mixed together within the catalyst body in any suitable configuration.

The catalyst particles in the catalyst bed 140 may be a function of and cooperative with the support ceramic balls in the sections 142, 144, or vice versa. In embodiments the catalyst particles are selected independently of the support ceramic balls.

Figure 6:
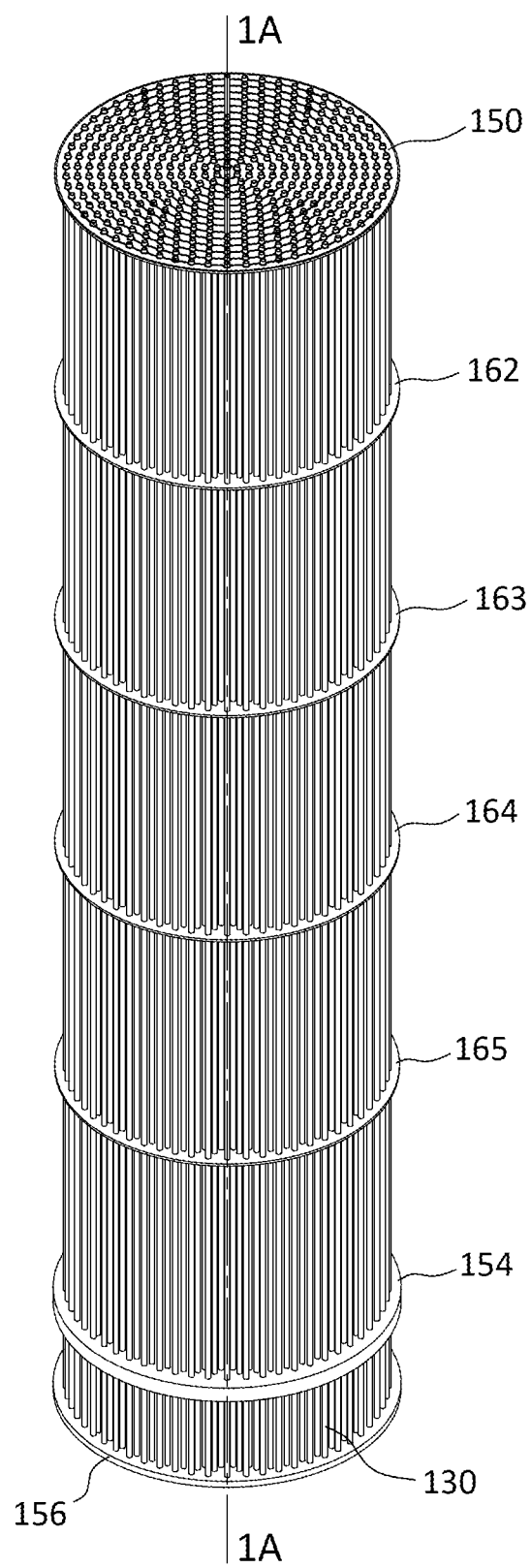
FIG. 6 is a perspective view of a tube bundle for use with a reactor according to the embodiment of FIG. 1A.
Figure 7:
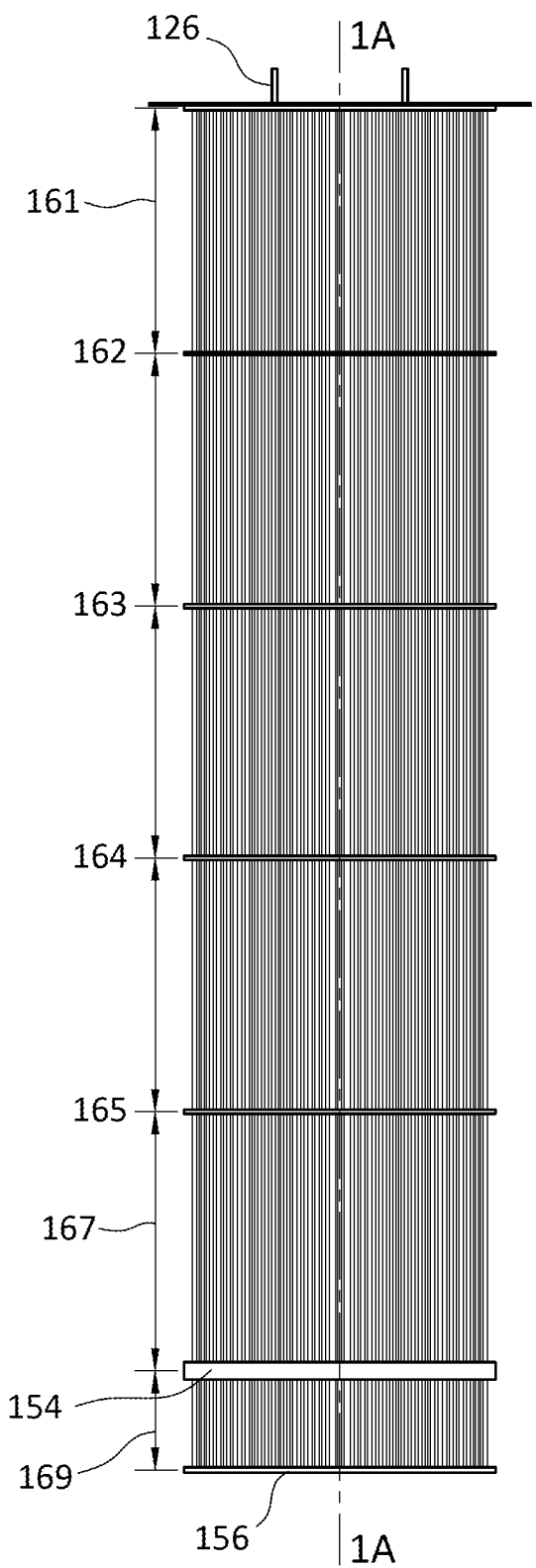
FIG. 7 is an elevational view of the tube bundle of the embodiment of FIG. 6.

A tube bundle 130 according to an embodiment is shown in FIGS. 6 and 7. The tube bundle 130 is configured to extend substantially longitudinally about the axis 1A-1A within the shell 102 and is maintained by, in order from top to bottom, a top plate and tube support plate 150, a plurality of tube support plates 162, 163, 164, 165, a catalyst support plate 154, and a gas inlet plate 156. A distance 161 between the top plate and tube support plate 150 and the tube support plate 162 and between the tube support plates 162, 163, 164, and 165 may be uniform along a length of the tube bundle 130. In embodiments the distance 161 may vary. A distance 167 between the tube support plate 165 and the catalyst support plate 154 may be greater than the distance 161. A distance 169 between the catalyst support plate 154 and the gas inlet plate 156 may be smaller than the distance 167. It will be appreciated that the depicted embodiment is merely exemplary and any arrangement of the tube bundle 130 may be used.

The tubes 131 may define a uniform thickness and diameter along a longitudinal length of the tube bundle 130. In embodiments, the tubes 131 have a tapered thickness along the length of the tube bundle, with increased thickness and/or diameter proximate one or more of the plates 150, 162, 163, 164, 165, 154, 156 in order to support the plates.

In embodiments, one or more of the tubes 131 of the tube bundle 130 may have an increased thickness relative to other tubes 131 for increased structural support. For example, tubes 131 that extend closer to a center or an outer edge of the tube bundle 130 may have an increased thickness relative to the other tubes of, for example, 10%, 20%, 25%, 33%, 50%, or any other suitable thickness. That is, the walls of such tubes 131 may have an increased thickness while in embodiments maintaining a same internal diameter. This advantageously allows the tubes 131 with the increased thickness to convey reactants while supporting the tube bundle 130, thereby freeing up cross-sectional area for increased catalyst loading and more evenly distributed catalyst relative to other structural arrangements.

In embodiments, the tubes 131 have a reduced thickness and/or increased diameter proximate a bottom portion of the reactor 100, for example to facilitate more-efficient heat transfer at the bottom portion of the reactor 100 compared to the top portion of the reactor 100. Alternatively, one or more of the tubes 131 of the tube bundle 130 may comprise internal tube rods configured to increase a velocity of the reactants being preheated therein. The internal tube rods may extend a partial or entire distance from a bottom of the tubes 131 to a top of the tubes 131.

The tube bundle 130 and the reactor 100 generally are advantageously configured for modularity in design and implementation. Whereas existing shell-and-tube-type reactors are not easily scalable due to the significant rework that must be completed to properly balance the tube length and diameters, the catalyst bed, the shell, and other components, the design of the reactor 100 advantageously allows for scaling up or down based on the arrangement of the concentric bands of tubes 131 on the tube bundle 130. The tube bundle 130 is arranged such that whether circumferential bands of tubes 131 are added (to increase the capacity of the reactor design for larger throughput or during a debottleneck effort) or removed (for scaling down the capacity of the reactor design), other geometric features of the reactor may remain unchanged. As a result extensive redesign work can be avoided.

The tube bundle 130 may be configured such that one or more geometric constraints or ratios are maintained in any design, regardless of whether the reactor and tube bundle are configured for reduced throughput or for increased throughput in various designs. To ensure that a tube density is improved, an average tube pitch (i.e. a center-to-center distance between tubes) of the tube bundle may be substantially constant throughout the tube bundle, with the circumferential bands and tubes defining the same being spaced so as to maintain a constant tube pitch.

As another example, the tube bundle 130 advantageously achieves a desired ratio of a cumulative cross-sectional area of the catalyst bed when viewing the reactor according to a plan view relative to a cumulative cross-sectional area of the tubes 131 (i.e. the total radial surface area of the tubes taken together) according to the same plan view. In embodiments, the ratio of the cumulative cross-sectional area of the catalyst relative to the cumulative cross-sectional area of the tubes is in a range between 2 and 20, more specifically between 5 and 12.

Regardless of a circumferential band of tubes 131 being added to or removed from the tube bundle 130 design, the cross-sectional area of the tubes 131 relative to the catalyst bed may be simply and easily adjusted so as to remain within a suitable bound, such that the performance of the reactor, and in particular its safety profile, are suitable. In an embodiment, adding or removing one or more circumferential bands of tubes may not substantially change the cumulative cross-sectional area of the catalyst relative to the cumulative cross-sectional area of the tubes. In other embodiments, the tube bundle 130 may be designed such that any other geometric or process-related parameter is targeted such that removal or addition of circumferential bands of tubes do not entail extensive redesign but rather allow an engineer to simply and easily adjust the reactor to a new, required capacity or other requirement. By providing a tube bundle 130 with the specified relation between the cross-sectional areas of the tubes and the catalyst bed, heat distribution is improved, which reduces the likelihood of runaway reactions by reducing hotspots and improving overall throughput through the reactor 100.

The reactor 100 may be controlled and maintained during operation to control one or more features of the catalyst bed 140 and/or the tube bundle 130. In some embodiments, the reactor 100 is configured to utilize the temperature measurement devices to evaluate a distribution of heat throughout the cross-sectional area of the catalyst bed. In particular, the reactor 100 may be controlled by assessing a radial temperature gradient within the reactor according to depth and/or assessing a growth of the gradient according to depth within the reactor 100 (from the top end 105 toward the bottom end 107).

Figure 12:
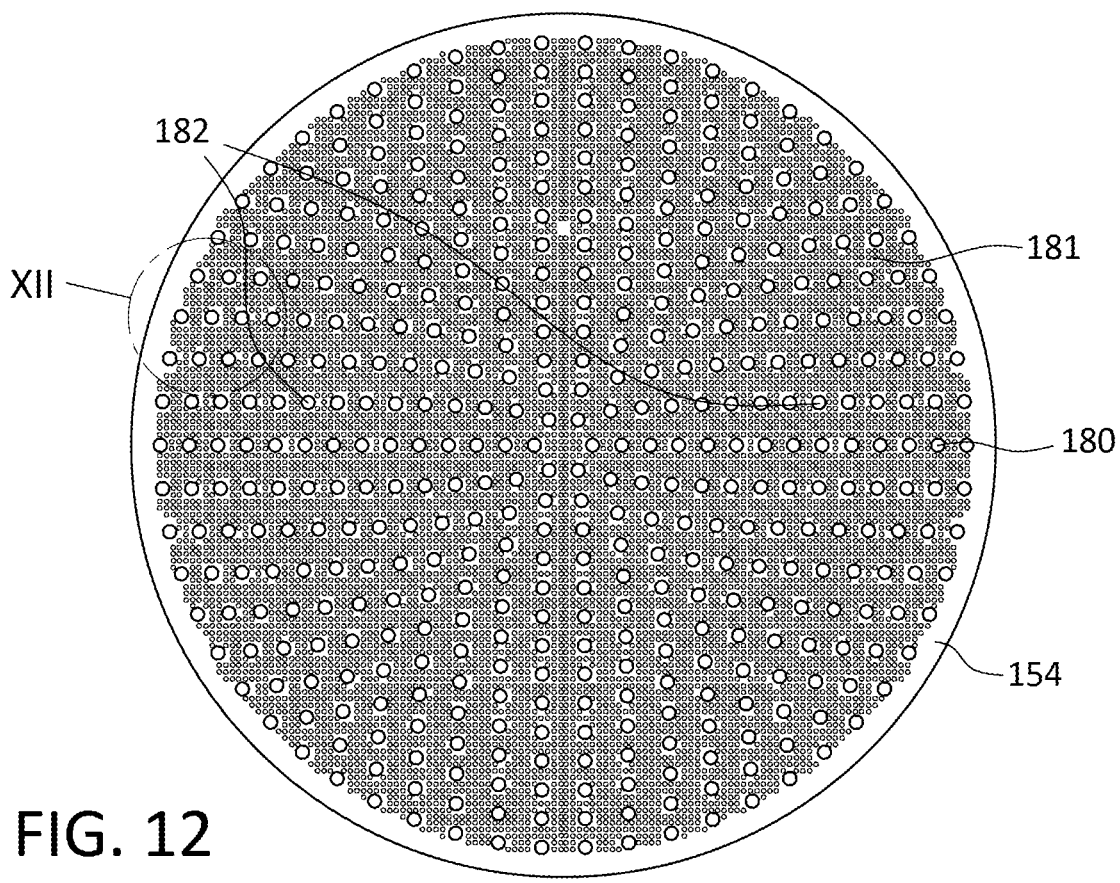
FIG. 12 is a plan view of a catalyst support plate according to the reactor of the embodiment of FIG. 1A.
Figure 13:
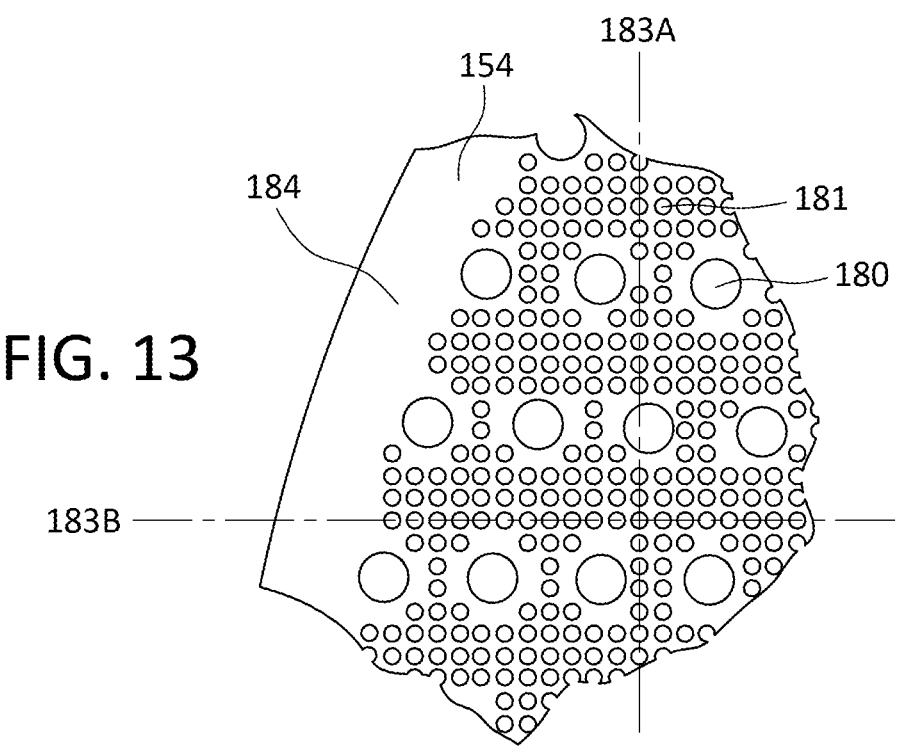
FIG. 13 is a close-up plan view of a catalyst support plate according to the detail XII.

Turning to FIGS. 12 and 13, the catalyst support plate 154 is configured to support a total height of the solid catalyst, such as a height of the sections 142, 144 combined with the height of the section 141. The catalyst support plate 154 further advantageously supports forces due to differential pressure over the catalyst bed 140. The catalyst support plate 154 may be arranged within the shell 102 proximate the catalyst unloading nozzle 116 and/or the hand hole 118. The catalyst support plate 154 may define one or more apertures 180, 181. The apertures 180, 181 may comprise or define apertures comprising a plurality of apertures of a first size corresponding to the apertures 180 and a plurality of apertures of a second size corresponding to the apertures 181, the apertures extending through at least part of a thickness of the catalyst support plate 154.

The first size of the apertures 180 may correspond to a circumference of at least one tube 131 of the tube bundle 130. In embodiments, the first size of the apertures 180 is larger than a circumference of the tubes 131 to allow for a degree of movement and/or thermal expansion of the tubes within the aperture 180. The apertures 180 may be defined through the catalyst support plate 154 according to an arrangement of the plurality of tubes 131 in the tube bundle 130. The second size of the apertures 181 may be smaller than the first size of the apertures 180, the second size of the apertures 181 serving to allow for flow of reactants, reaction products, and reaction byproducts therethrough en route to the outlet nozzle 124.

In embodiments, one or more of the apertures 180 may define a terminus for a temperature measurement device. The apertures 182 may be sized and configured to receive a thermocouple insertion tube 126 and to terminate an extension of the thermocouple insertion tubes 126 (FIG. 7). The apertures 182 may in embodiments extend only partly into the thickness of the catalyst support plate 154. In embodiments the thermocouple insertion tubes 126 may be welded to the catalyst support plate 154 and plugged thereat. The tubes 131 may not be welded to the catalyst support plate 154 to allow for the effects of thermal expansion.

The size of the apertures 181 and/or the average distance between the apertures 181 may be a function of the thickness of the catalyst support plate 154, such that the size of the apertures 181 is proportional to a thickness of the catalyst support plate 154 and/or the distance between the apertures 181 is inversely proportional to the thickness of the catalyst support plate 154. That is, the greater the thickness of the catalyst support plate 154, the greater the diameter of the apertures 181 and/or the smaller the distance between the apertures 181. In embodiments, the catalyst support plate 154 may have a thickness of between 20 and 500 mm, more specifically between 50 and 300 mm, and in embodiments 110 mm, while the apertures 181 may have a diameter of 1-50 mm, more specifically 5-25 mm, and in embodiments 10 mm.

As seen in the close-up view of FIG. 13, the apertures 180 may extend in a pattern or arrangement corresponding to an arrangement of tubes 131 in the tube bundle 130 as will be discussed in greater detail herein. The apertures 181 may extend between each of the apertures 180. The apertures 181 may define any suitable pattern or arrangement, such as an extension direction 183A and/or a transverse extension direction 183B, the extension directions 183A, 183B defining straight lines. Other patterns or arrangements of the apertures 181 are contemplated within the scope of the disclosure. The apertures 181 may be spaced apart from each other by any suitable distance, including in embodiments by a distance of 1-30 mm from center to center of adjacent apertures 181, more specifically from 5-20 mm from center to center, and in embodiments 15 mm from center to center of adjacent apertures 181 along one or both of the directions 183A, 183B. The distance from center to center of adjacent apertures 181 need not be uniform across an entirety of the surface of the catalyst support plate 154 but rather may vary as suitable.

The catalyst support plate 154 may define at an outer periphery a band 184 of material forming the catalyst support plate 154 that does not define any of the apertures 180, 181. The band 184 may extend partially or wholly about the periphery of the catalyst support plate 154 and advantageously facilitates welding or other suitable attachment of the catalyst support plate 154 to the interior surface of the shell 102. In embodiments, the band 184 may extend into and then be welded to a recess defined by the inner surface of the shell 102. The band 184 may extend any suitable distance such as 5 mm radially.

Figure 11:
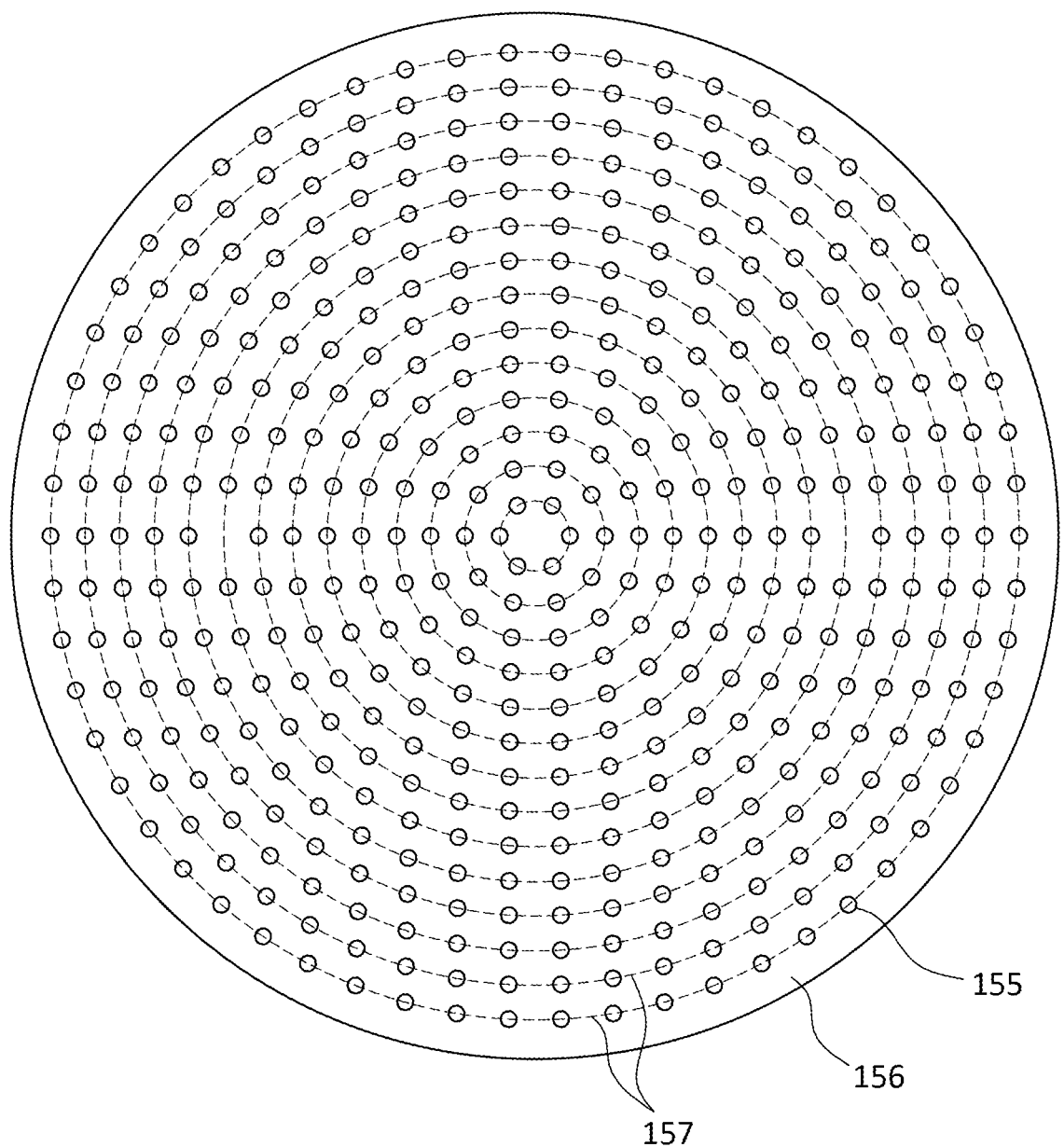
FIG. 11 is a plan view of a gas inlet plate according to the reactor of the embodiment of FIG. 1A.

Turning to FIG. 11, the gas inlet plate 156 may be arranged below the catalyst support plate 154, and may comprise a plurality of apertures 155 defined through at least part of a thickness of the gas inlet plate 156. The plurality of apertures 155 may be circular apertures defined through the gas inlet plate 156 according to the arrangement of the plurality of tubes 131 of the tube bundle 130, and aligning with an arrangement of the apertures 180 of the catalyst support plate 154. In an embodiment, the gas inlet plate 156 is substantially solid and devoid of openings outside of the plurality of apertures 155 so as to force the incoming reactants into the tubes 131. The plurality of tubes 131 may be seal welded and/or strength welded to the gas inlet plate 156. It will be appreciated that where a component is discussed herein as being welded to another component, seal welding, strength welding, a combination thereof, or any other type of attachment is contemplated.

Figure 8:
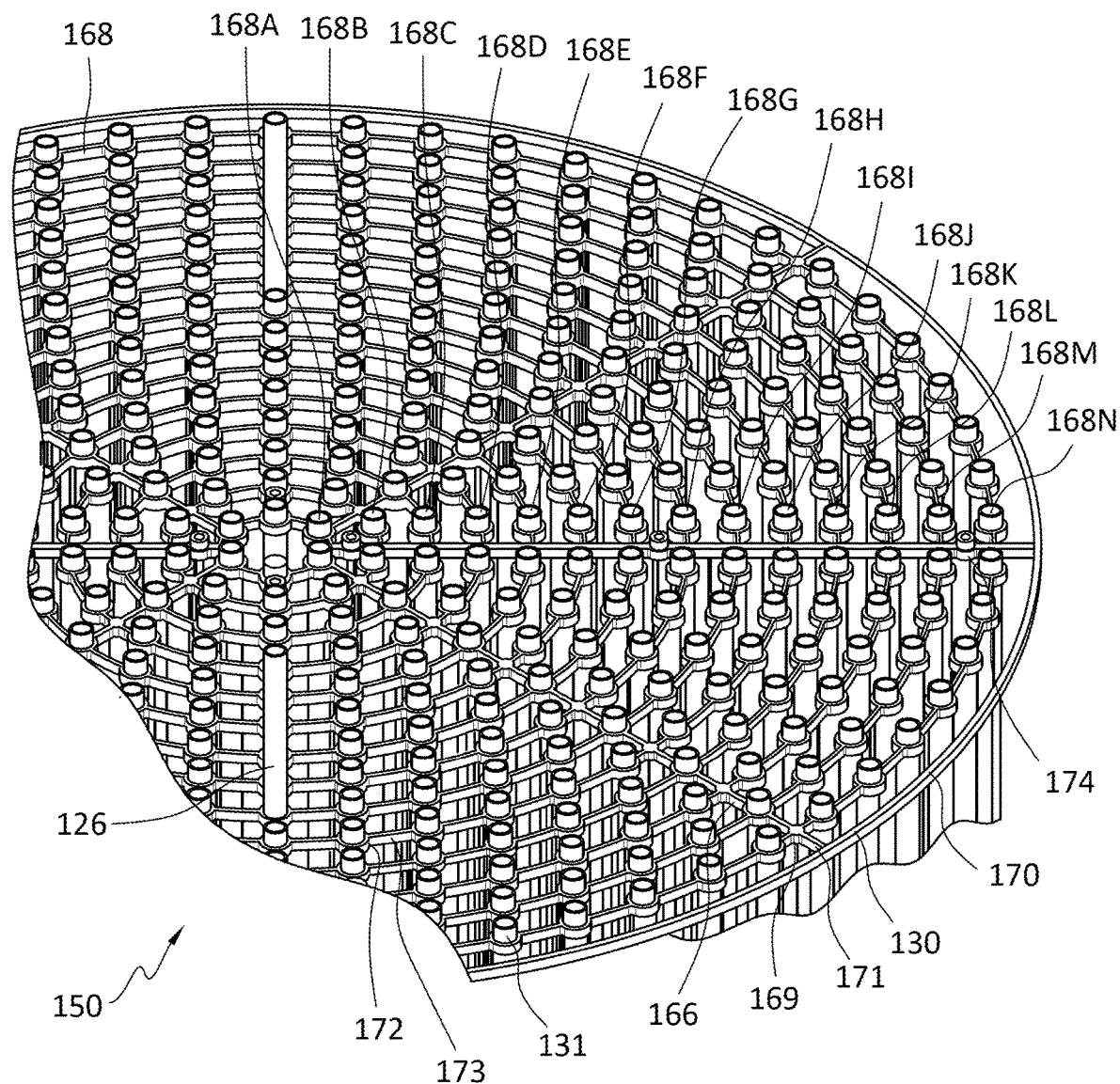
FIG. 8 is a perspective view of a tube bundle and tube support plate according to the embodiment of FIG. 6.
Figure 9:
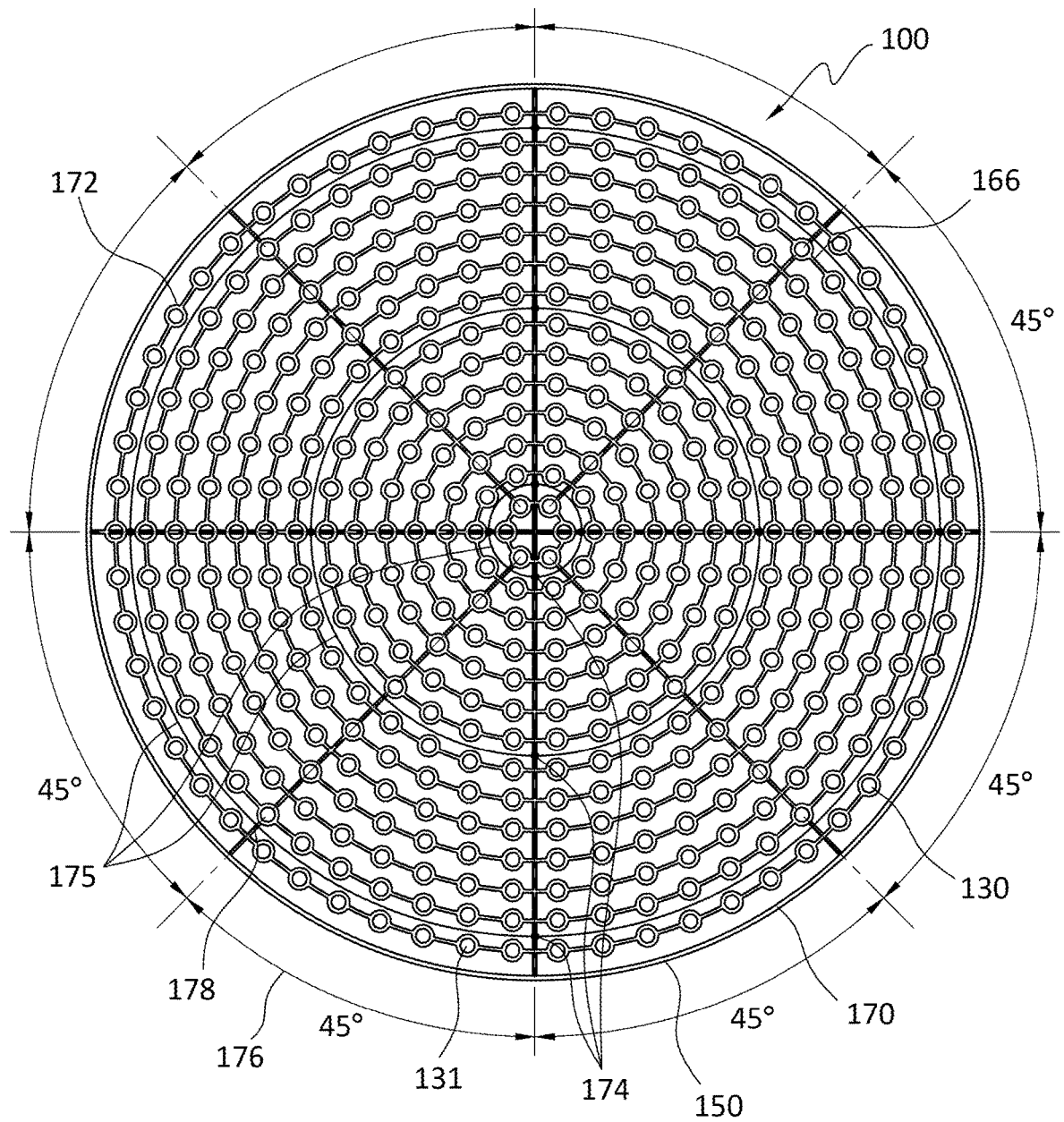
FIG. 9 is a plan view of a top and feed tube support plate according to the reactor of the embodiment of FIG. 1A.

Turning to FIGS. 8-9, the reactor 100 may further comprise at least one tube support plate 150, 162, 163, 164, 165 which may be arranged longitudinally spaced apart along an axial or longitudinal length of a tube bundle 130. The tube support plates 150, 162, 163, 164, 165 are shown and described, but it will be appreciated that more or fewer support plates may be provided. The top and feed tube support plate 150 may be substantially the same as the tube support plates 162, 163, 164, 165 and may include or omit one or more features. For example, the top and feed tube support plate 150 may have the same features as the tube support plates 162, 163, 164, 165 and may further include one or more spacers configured to cooperate with a top plate, as will be described in greater detail below.

The tube support plate 150, 162, 163, 164, 165 may comprise at least one circumferential band 168 configured to maintain a position of the at least one tube 131. The at least one circumferential band 168 comprises at least one bracket 172 configured to extend about a portion of a tube 131 of the tube bundle 130. In embodiments, the at least one bracket 172 extends about an entirety of the tube 131. The bracket 172 may be configured to releasably attach to the tube 131.

In embodiments, the bracket 172 may extend about only a portion rather than an entirety of the tube. The bracket 172 may advantageously cooperate with a beam 173 that extends between the bracket 172 and an adjacent bracket 172 attached to an adjacent tube 131. The bracket 172 may be connected releasably or non-releasably with the beam 173 and may define a filleted connection, for example. A circumferential band 168 may be defined by a series of connected brackets 172 and beams 173 defining a substantially circumferential arrangement with corresponding tubes 131.

The circumferential band 168 may be concentrically arranged with adjacent circumferential bands 168 of the tube support plate 150, 162, 163, 164, 165, with the circumferential bands 168 optionally centered on the longitudinal axis 1A-1A of the reactor. The cooperation of brackets 172, beams 173, radial struts 166, and circumferential bands 168 together define a tube support plate. While the circumferential bands 168 have been shown and described, it will be appreciated that any suitable configuration may be used, including asymmetric, offset, or non-circumferential arrangements. While the cooperation of various components is described as defining a tube support plate, it will be appreciated that a tube support plate may take any suitable configuration and is not limited hereby.

The at least one tube support plate 150, 162, 163, 164, 165 defines at least one radial strut 166 connected to the at least one circumferential band 168 at an attachment point 169 and/or to an outer support band 170 at an attachment point 171. The tube support plate may define a plurality of radial struts 166 arranged radially symmetrically, for example at 22.5° increments, at 30° increments, at 45° increments, at 90° increments, at 120° increments, at 180° increments, another increment evenly divisible by 360°, or otherwise. In other embodiments, the radial struts 166 are arranged asymmetrically in any suitable manner.

Figure 10A:
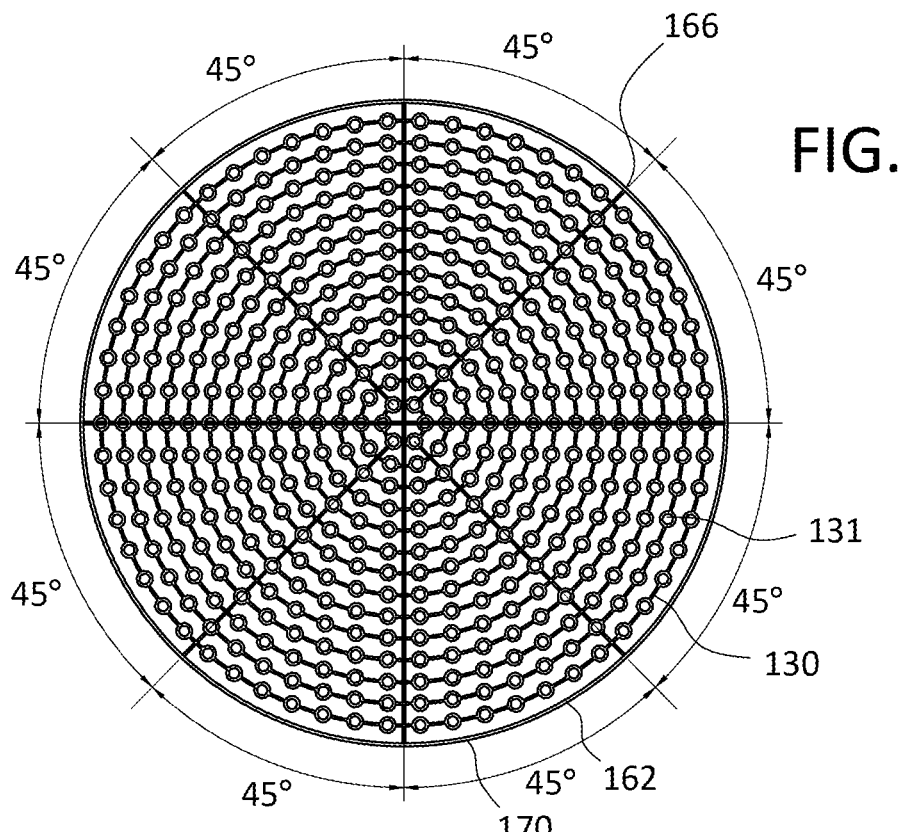
FIG. 10A is a plan view of the tube support plate according to the embodiment of FIG. 6.

The outer support band 170 may define a substantially continuous band of support material, such as stainless steel, that provides sufficient rigidity, strength, and/or support to the tube support plate, and/or that facilitates attachment of the outer support band 170 to an inner surface of the reactor shell 102. While eight radial struts 166 are shown and described regarding the embodiment of FIGS. 9 and 10, it will be appreciated that more or fewer radial struts 166 may be provided, and that all of the tube support plates 150, 162, 163, 164, 165 need not have a same number or arrangement of radial struts or other components.

The radial struts 166 may extend straight outwardly from a center of the tube support plate to the outer support band 170, or may define a curved, bent, tortuous, or other configuration. The radial struts 166 may be formed of any suitable material, such as stainless steel, and may define heat-resistance properties to retain desired stiffness and strength in the reactor conditions. The radial struts 166 advantageously define attachment points 169 between the circumferential bands 168 and the radial struts 166. The attachment points 169 may be releasable or non-releasable, and may define any suitable connection, such as being welded together or being attached by a suitable fastener. The tube support plate may be configured to move with the tubes 131 by thermal expansion and contraction, and may be formed of high temperature-resistance materials, such as steel (e.g., stainless steel), ceramics, polymeric materials, composite materials, or otherwise.

In embodiments, the tube support plate 150, 162, 163, 164, 165 may be fabricated using any suitable means. In embodiments, the tube support plate 150, 162, 163, 164, 165 is formed from a single, solid plate from which material is removed for example by water jet cutting. In other embodiments, the radial struts and circumferential bands are independently fabricated and assembled to form the tube support plates.

The top and feed tube support plate 150 may additionally define one or more spacers 174 on a top surface thereof. The spacers 174 may be attached to one or more structures of the top and feed tube support plate 150 in any suitable manner, including by welding. The spacers 174 may extend a predetermined height and may define an aperture within a center portion thereof. The aperture may comprise one or more threadings configured to matingly engage with one or more threadings of a fastener, as will be discussed in greater detail herebelow regarding the top plate 190. The spacers 174 may extend about the top and feed tube support plate 150 in any suitable arrangement and in any suitable number.

For instance, the spacers 174 may define three concentric ring patterns 175 (FIG. 9) about the top and feed tube support plate 150 as the spacers 174 attach to radial struts 166. In an embodiment, the spacers 174 extend along four of the radial struts 166 between the first and second circumferential bands, between the seventh and eighth circumferential bands, and between the thirteenth and fourteenth circumferential bands. A total of four spacers 174 may be arranged on each of the concentric ring patterns 175, such that a corner portion of each segment of the top plate 190 may be fastened thereto, as will be described herebelow.

The arrangement of the radial struts 166 advantageously provides a secure attachment of the tubes 131 of the tube bundle 130 while minimizing interference with the distribution of catalyst as the catalyst is loaded from the top portion 105 of the reactor 100. For example, as the catalyst particles are poured into the shell 102, the radial struts 166 are configured to minimize uneven distribution of the catalyst. In embodiments, the radial struts 166 of adjacent tube support plates 162, 163, 164, 165 may align axially along the longitudinal extension length of the reactor 100.

Figure 10B:
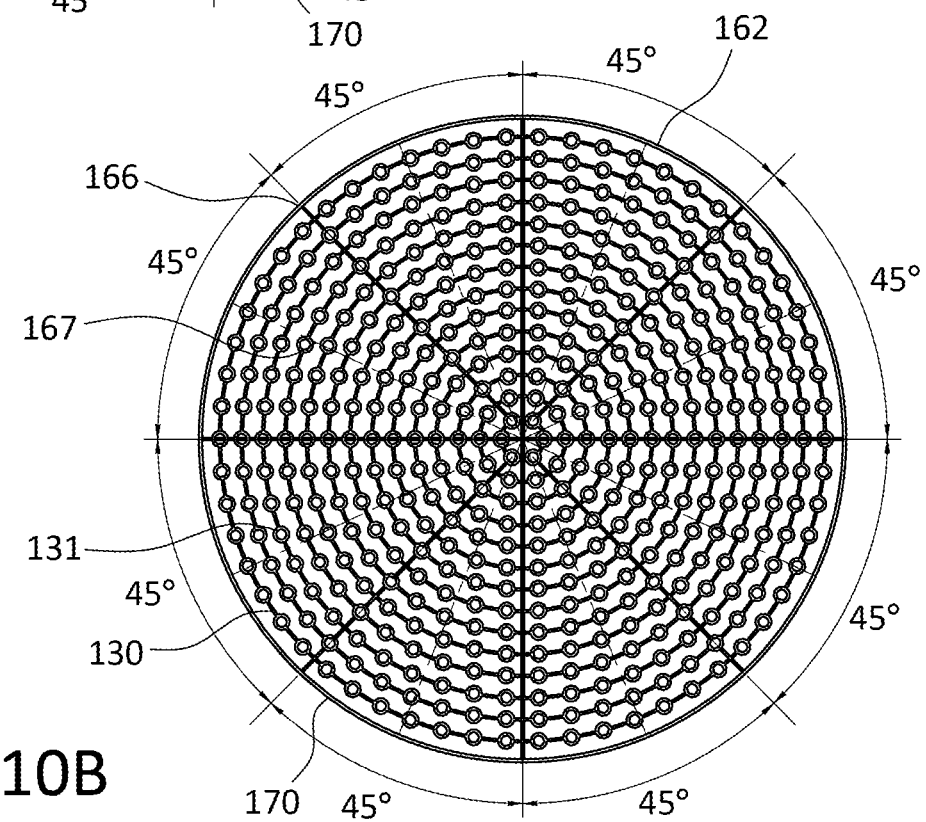
FIG. 10B is a plan view of a tube support plate according to another embodiment.

In other embodiments, as shown in FIG. 10B, the radial struts 167 of adjacent tube support plates may be offset from the radial struts 166 to promote even distribution of the catalyst during loading. The degree of offset may be any suitable degree. In embodiments, the radial struts 167 are offset by a distance corresponding to half the angular distance between the radial struts 166. In the embodiment of FIG. 10B, the radial struts 166 are offset by 45° from each other, and the offset of the radial struts 167 is 22.5°. Subsequent tube support plates may alternate in arrangement. The radial struts 166 of adjacent tube support plates may be offset down a longitudinal length of the reactor so as to define a spiral or helix pattern. The depicted embodiment is exemplary, and any other arrangement may be used as suitable.

The tube bundle 130 may be arranged such that an innermost circumferential band 168A of the at least one tube support plate comprises six brackets configured respectively to correspond to a ring of six innermost tubes of a first size. The first size may be, for example, 0.5-3 mm in diameter, more specifically 1-2 mm in diameter, and in embodiments 1.5 mm. A second circumferential band 168B of the at least one tube support plate comprises 10 brackets configured respectively to correspond to a ring of 10 tubes of the tube bundle of the first size. A third circumferential band 168C of the at least one tube support plate comprises 14 brackets configured respectively to correspond to a ring of 14 tubes of the tube bundle of a second size. The second size may be, for example, 0.5-5 mm in diameter, more specifically 1-4 mm, and in embodiments 2.5 mm.

A fourth circumferential band 168D of the at least one tube support plate comprises 18 brackets configured respectively to correspond to a ring of 18 tubes of the tube bundle of the first size. A fifth circumferential band 168E of the at least one tube support plate comprises 22 brackets configured respectively to correspond to a ring of 22 tubes of the tube bundle of the first size. A sixth circumferential band 168F of the at least one tube support plate comprises 26 brackets configured respectively to correspond to a ring of 26 tubes of the tube bundle of the first size.

A seventh circumferential band 168G of the at least one tube support plate comprises 30 brackets configured respectively to correspond to a ring of 30 tubes of the tube bundle of the second size. An eighth circumferential band 168H of the at least one tube support plate comprises 34 brackets configured respectively to correspond to a ring of 34 tubes of the tube bundle of the first size. A ninth circumferential band 168I of the at least one tube support plate comprises 36 brackets configured respectively to correspond to a ring of 36 tubes of the tube bundle of the first size. A tenth circumferential band 168J of the at least one tube support plate comprises 42 brackets configured respectively to correspond to a ring of 42 tubes of the tube bundle of the first size.

An eleventh circumferential band 168K of the at least one tube support plate comprises 46 brackets configured respectively to correspond to a ring of 46 tubes of the tube bundle of the second size. A twelfth circumferential band 168L of the at least one tube support plate comprises 50 brackets configured respectively to correspond to a ring of 50 tubes of the tube bundle of the first size. A thirteenth circumferential band 168M of the at least one tube support plate comprises 54 brackets configured respectively to correspond to a ring of 54 tubes of the tube bundle of the first size. A fourteenth circumferential band 168N of the at least one tube support plate comprises 58 brackets configured respectively to correspond to a ring of 58 tubes of the tube bundle of the second size.

While the first through fourteenth circumferential bands have been shown and described, it will be appreciated that the reactor embodiments of the present disclosure advantageously facilitate a modular reactor construction that accommodates different throughput requirements of different facilities better than existing reactor designs. As needed, for example, an engineer may modify the depicted tube bundle 130 to have more, fewer, and/or different circumferential bands. In order to scale up the tube bundle 130 and the reactor 100 as a whole to accommodate a higher yearly capacity of a plant, such as during a debottlenecking effort, an additional circumferential band may be added to increase the number of tubes and expand the tube bundle outwardly in a simple modification. For example, the attachments 171 between the radial struts 166 and the outer band 170 may be released such that an additional circumferential band may be added to the tube support plate, with the outer band 170 replaced about the new circumferential band. To this end, the outer band 170 may be configured to have an expandable circumference.

Conversely, to scale down the reactor 100, a circumferential band, such as an outermost circumferential band, may be removed to reduce the size of the tube bundle so as to fit a smaller reactor shell and/or to yield a correspondingly lower yearly plant capacity. This may be done, for example, by detaching the attachments 169 between circumferential bands and the radial struts.

Moreover, the arrangement of the circumferential bands as shown allows for the addition or removal of circumferential bands and the accompanying brackets and tubes while accommodating the structure of the radial struts. As seen, the circumferential bands increase in number of brackets and tubes such that the tubes are positioned in a substantially even distribution and with sufficient space between the tubes to allow for catalyst and reactant to pass therebetween and for the circumferential bands to be added or removed without disrupting the design of the radial struts and the tube support plate generally.

In an embodiment, the ninth circumferential band 168I (or any other) of the at least one tube support plate further comprises brackets 172 corresponding to at least one thermocouple insertion tube 126, the at least one thermocouple insertion tube 126 being of the first tube size. The provision of brackets 172 for the thermocouple insertion tube 126 allows for temperature measurement devices to be inserted into the tube bundle, preferably into a region of the tube bundle where the temperature measurement device will be surrounded by catalyst and tubes, for accurate temperature readings along a longitudinal length of the reactor.

The top and feed tube support plate, similar to the tube support plates 162, 163, 164, 165, may comprise one or more radial struts 166, an outer band 170, and one or more brackets 172 configured to engage with and/or surround a tube 131 of a tube bundle 130. The radial struts 166 of the top and feed tube support plate 150 may be arranged analogous or corresponding to the struts 166 of the feed tube support plates 162, 163, 164, 165 and may be divided axially by a suitable angle 176 (FIG. 9), such as 45°. It will be appreciated that other angles or arrangements are contemplated by the present disclosure.

The brackets 172 of the top and feed tube support plate 150 may constitute or extend proximate a terminus of the tubes 131, with the pre-heated reactants exiting the tubes 131 thereat and then flowing in the second direction F2 downwardly. The thermocouple insertion tubes 126 may extend a distance above a topmost distance or extent of the tubes 131, this facilitating easier insertion of the temperature measurement devices from the thermocouple port 106 to the thermocouple insertion tube 126. As with the tube support plates 162, 163, 164, 165, the top and feed tube support plate 150 may be configured to be expanded or decreased in size as suitable for a desired capacity of the reactor 100.

The arrangement of the tube bundle 130 and the tube support plates 150, 162, 163, 164, 165 may advantageously account for heat transfer and reactor kinetics of the reactor.

Figures 14, 15:
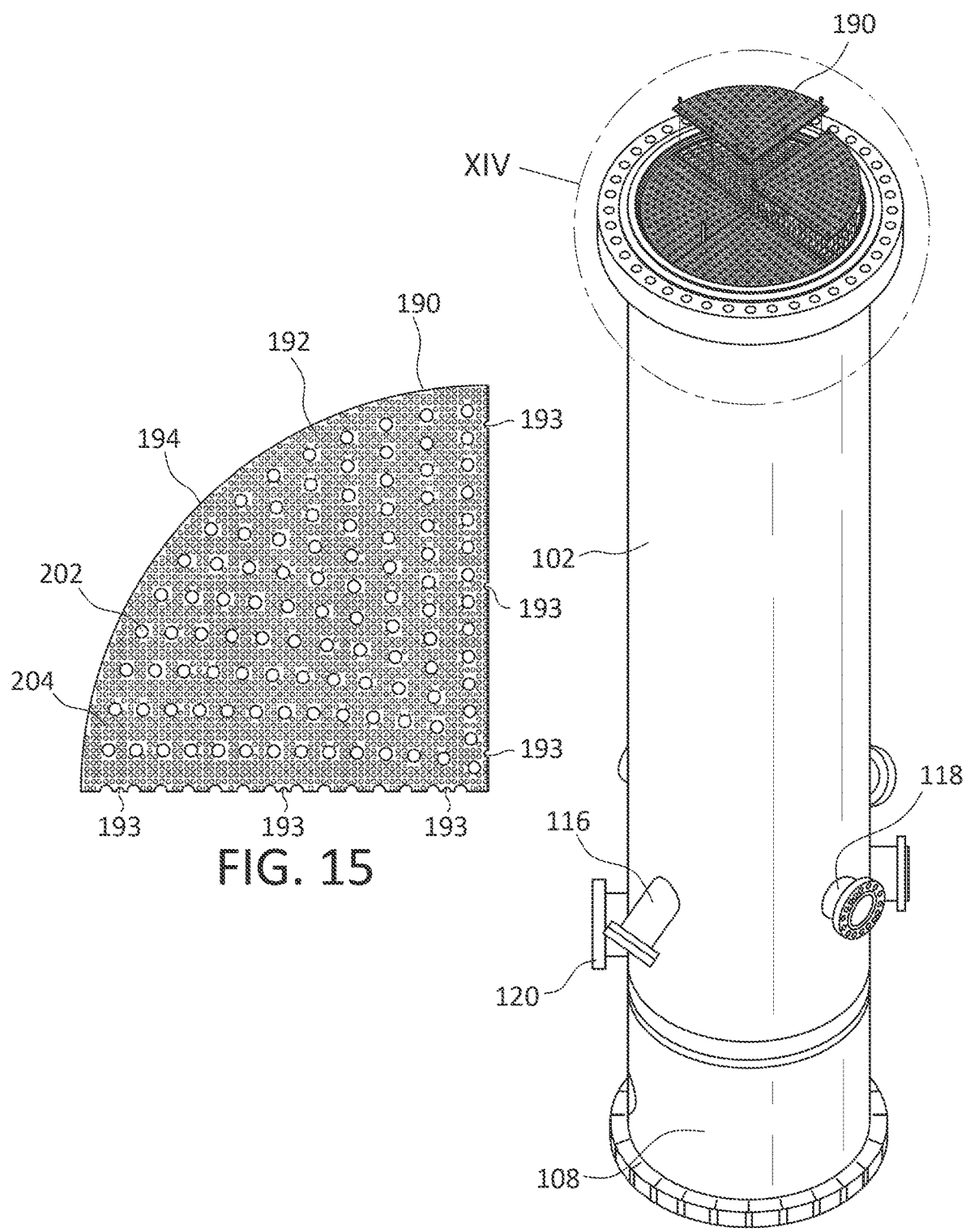
FIG. 14 is a perspective exploded view of a top plate and reactor according to the embodiment of FIG. 1A.
FIG. 15 is a plan view of the top plate of the embodiment of FIG. 14.
Figure 16:
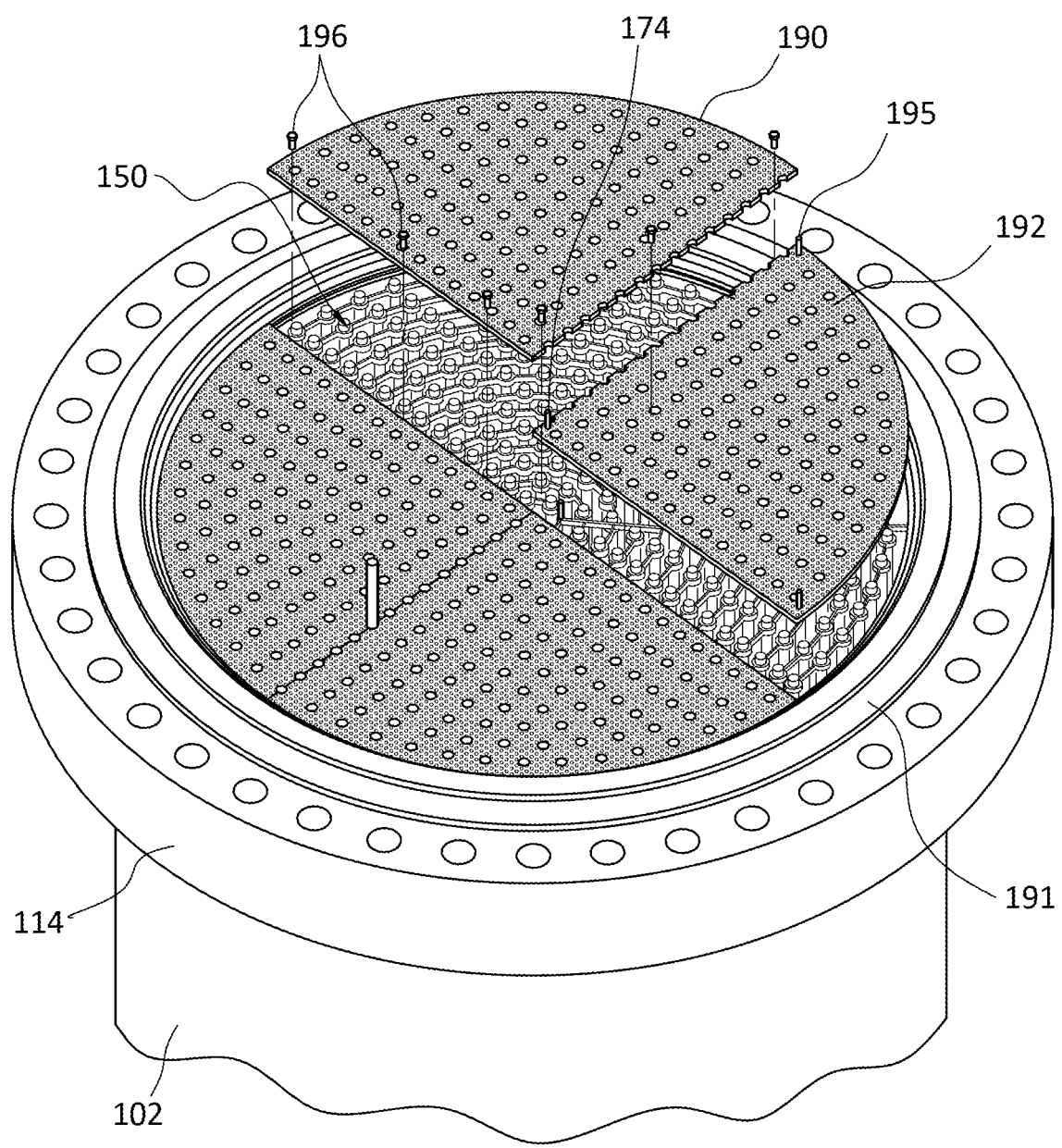
FIG. 16 is a close-up perspective exploded view of a top plate for use with the reactor of the embodiment of FIG. 1A according to the view XIV.

Turning to FIGS. 14-16, a top plate 190 is shown. The top plate 190 may be configured to be installed a top or above the top and feed tube support plate 150. The top plate 190 may be modular in construction and define four distinct segments 192 surrounded by a flange 191. The top plate 190 may define a plate edge 194, one or more tube holes 202 defined through at least a partial thickness of the plate 190, and one or more gas apertures 204 defined through at least a partial thickness of the plate 190. The tube holes 202 may be configured to align generally with an arrangement of the tubes 131 of the tube bundle 130 and facilitate passage of pre-heated reactants out of the tubes 131 into the space 113 (FIG. 5B) of the reactor 100.

The gas apertures 204 facilitate passage of the pre-heated reactant into the catalyst bed 140 and ensure proper flow distribution. The top plate 190 may be configured to create a small pressure drop to make the flow entering the catalyst bed as uniform as possible. The top plate 190 is advantageously configured to achieve improved uniformity of flow distribution using a simplified design as shown and described relative to existing approaches which may utilize heavy and/or complicated designs that are difficult and/or costly to manufacture and/or to manipulate for maintenance purposes.

As the top plate 190 may extend outwardly to the flange 191, the gas apertures 204 may extend substantially to the edge 194 without leaving a gap as in the catalyst support plate 154. The top plate 190 may have a reduced thickness compared to the catalyst support plate 154. In embodiments, the top plate 190 has a thickness of between 1 and 25 mm, more specifically between 5 and 15 mm, and in embodiments 8 mm.

The top plate 190 is configured to be removably attached to the shell 102 and/or to the top plate and tube support plate 150 by any suitable mechanism, such as by the use of fasteners 196 that cooperate with corresponding apertures 193 (FIG. 15) at the edge of each section of the plate 190. The fasteners 196 of the top plate 190 may cooperate with one or more of the spacers 174 extending between the top plate 190 and the top and feed tube support plate 150, and which may be welded, for example tack welded, to the top and tube support plate 150.

In embodiments, the spacers 174 may have a height and/or circumference sufficient to receive a mating end of the fastener 196 within a track or recess defined through a portion of a thickness of the spacer 174, this allowing a robust attachment of the top plate 190 onto the top and feed tube support plate 150. The height of the spacer 174 may be between 1 and 30 mm, more specifically between 5 and 20 mm, and in embodiments 15 mm. The spacer 174 may be welded onto a radial strut 166, a circumferential band 168, a bracket 172, or otherwise. As seen, the fasteners 196 and the corresponding spacers 174 may be located such that a fastener and spacer 196, 174 is provided in each corner and along interior edges of a section 194 of the top plate 190.

The top plate 190 may further comprise or cooperate with one or more load rings 195. The load rings 195 may be any suitable component configured to facilitate positioning and/or removal of the section 194 of the top plate 190. The load rings 195 may attach through one or more of the gas apertures 204 or at any other suitable location and define a component for removably securing to and manipulating the top plate 190. In embodiments the load rings 195 are configured to allow an operator to grasp the top plate 190 with a tool for lifting the top plate 190 away from the reactor shell 102.

By providing the top plate 190 in a modular fashion, with the distinct sections 194, the top plate 190 is more easily removable and replaceable during maintenance operations without sacrificing the ability of the top plate 190 to distribute the reactants and secure the catalyst bed 140. The modular construction of the top plate 190 further makes the manufacturing process less costly and complex, as identical sections 192 may be manufactured rather than plates 190 of unitary construction. One benefit of the arrangement of the top plate 190 is the ability for a plant worker to stand on one of the sections 194 of the top plate 190 while loading catalyst through the opening provided by a section 194 that has been removed.

Figure 17:
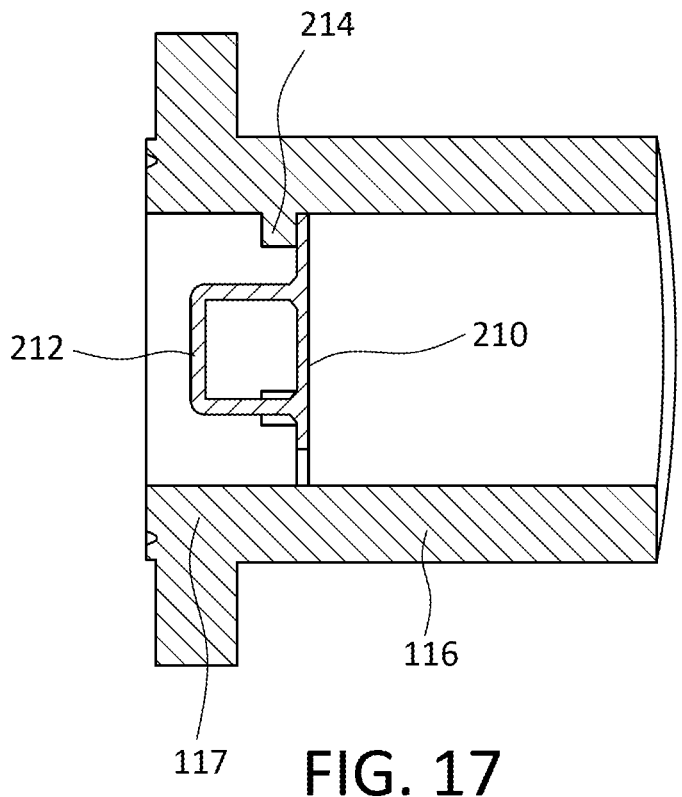
FIG. 17 is an elevational cutaway view of a retaining plate for use with a nozzle of a reactor according to the embodiment of FIG. 1A taken along the line 16A-16A.
Figure 18:
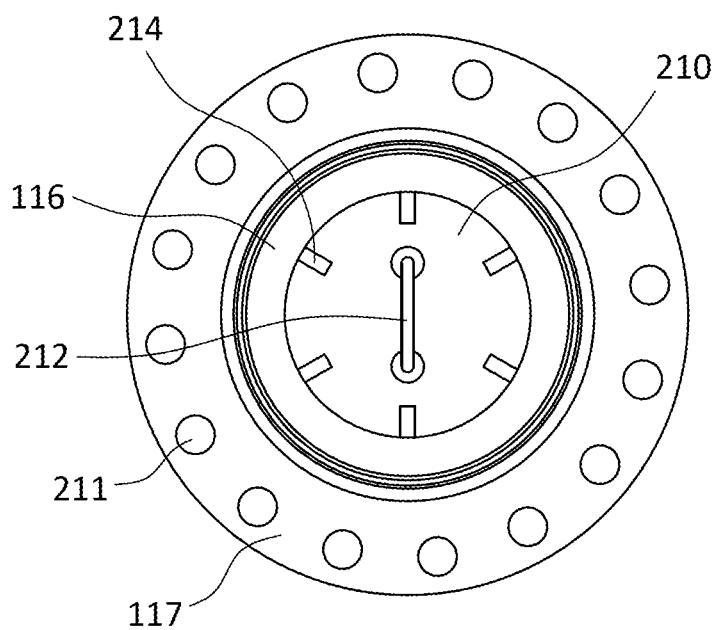
FIG. 18 is an elevational view of the retaining plate and nozzle according to the embodiment of FIG. 17.
Figure 19:
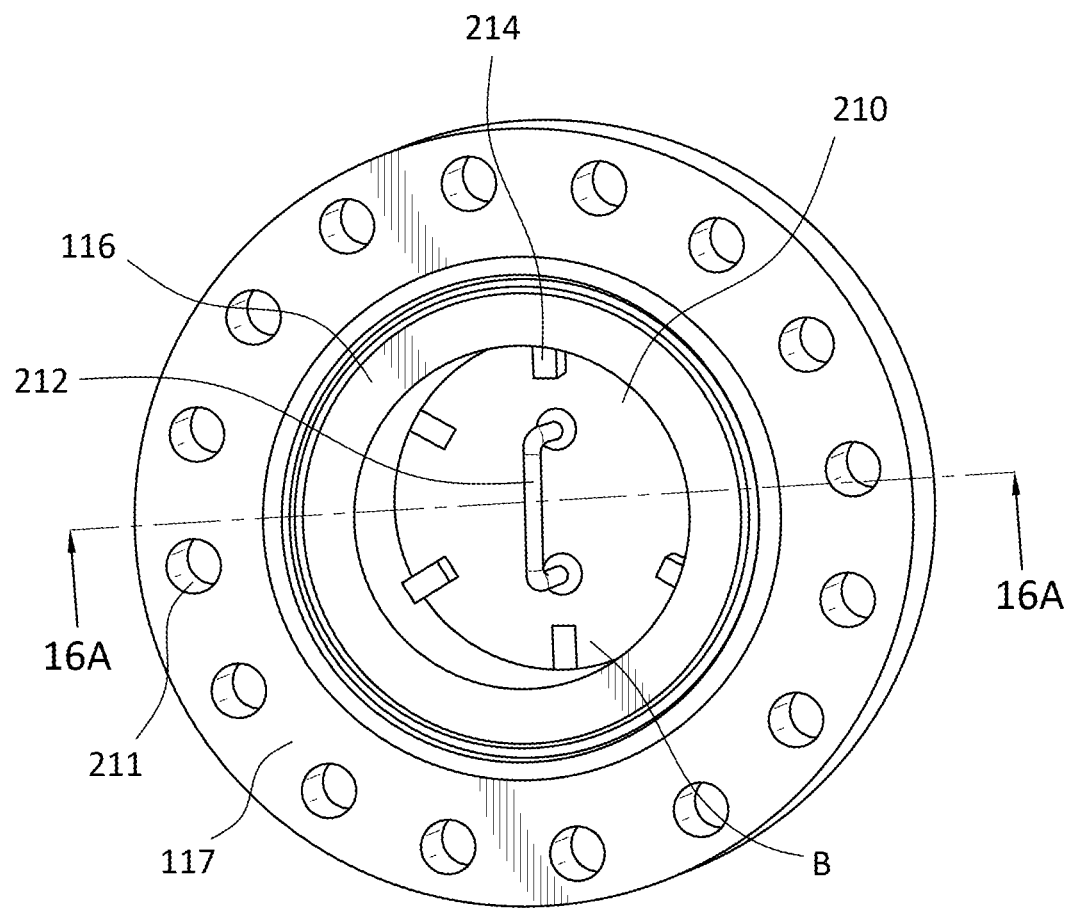
FIG. 19 is a perspective view of the retaining plate and nozzle according to the embodiment of FIG. 17.

Turning to FIGS. 17-19, a retaining plate 210 for use with one or more nozzles of the reactor 100 is shown and described. The retaining plate 210 may secure the catalyst unloading nozzle 116 and/or the hand hole 118. The retaining plate 210 may comprise a handle 212 and is configured to cooperate with a lip 214 defined by the nozzle 116. In embodiments, the nozzle 116 defines a plurality of lips 214 arranged circumferentially about an opening of the nozzle in any suitable pattern, with the retaining plate 210 configured to abut an inner surface of the lip 214 as seen in FIG. 17. In embodiments, the lips 214 are spaced apart by an angle, such as 15°, 20°, 30°, 45°, 60°, 90°, or otherwise. The arrangement of the lips 214 may be symmetric or asymmetric. The flange 117 of the nozzle 116 may define one or more apertures 211 through which suitable fasteners may be received to connect the nozzle 116 to a suitable spool.

In particular embodiments, the plurality of lips 214 do not extend about a bottommost section B of a circumferential aperture defined by the catalyst unloading nozzle 116 or the hand hole 118. Rather, as seen in FIG. 19, the bottommost section B is unobstructed such that catalyst particles may flow freely under the effects of gravity during catalyst unloading. The arrangement of the retaining plate 210 advantageously prevents the catalyst from flowing too fast during catalyst unloading.

Figure 20:
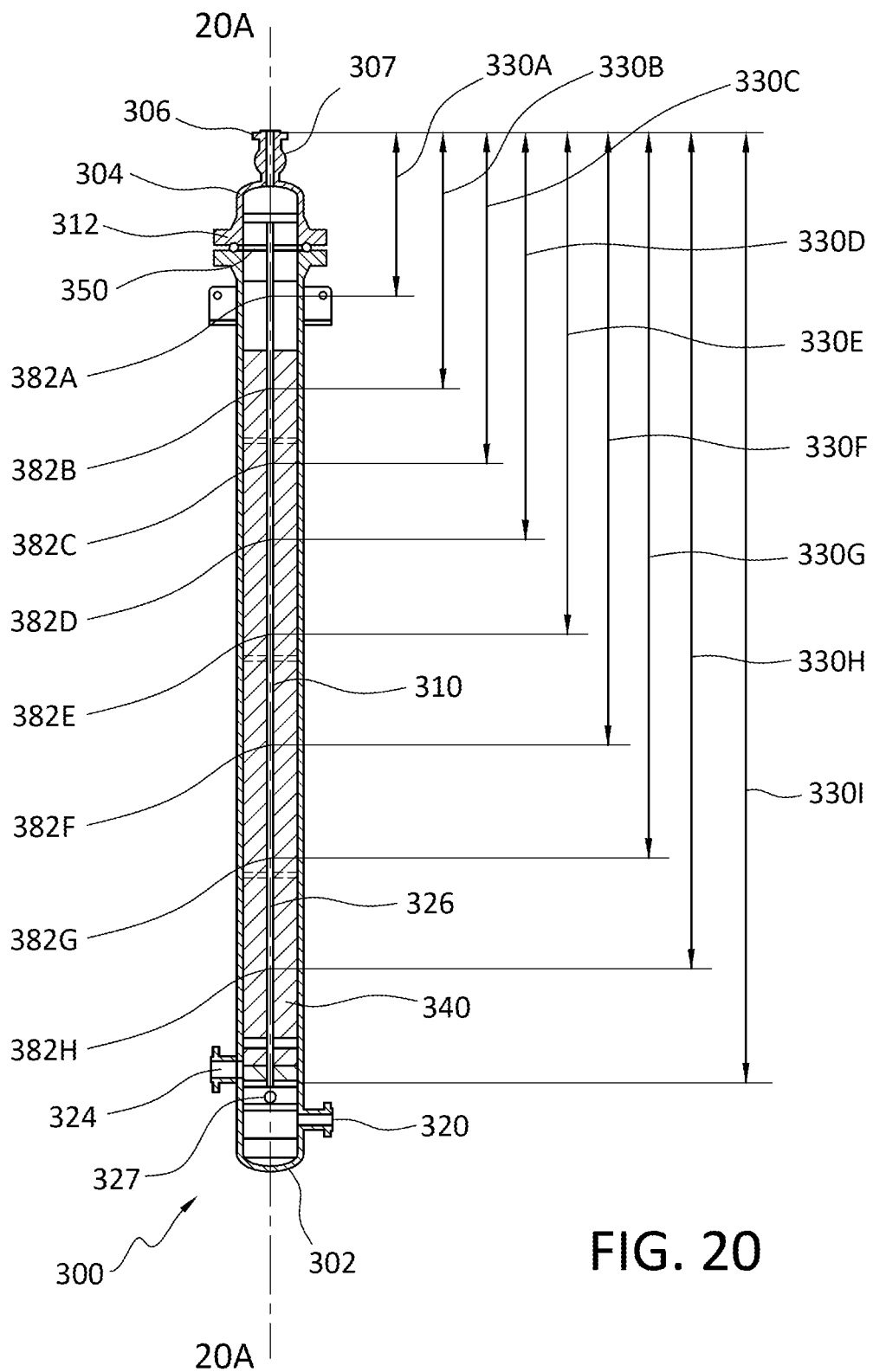
FIG. 20 is a cutaway elevational view of a reactor, catalyst bed, and thermocouple insertion tube according to another embodiment.

Turning to FIG. 20, a reactor 300 according to an embodiment is shown and described. The "300" series reference numbers may include similar or identical features to those already described with "100" series reference numbers. The reactor 300 comprises a shell 302 in which a tube bundle having a top plate 350 as described above may be received and secured, and defines an inlet nozzle 320 and an outlet nozzle 324. The shell 302 may further comprise or cooperate with a domed top portion 304 defining and/or supporting a thermocouple insertion nozzle 306. The domed top portion 304 may be secured to the shell 302 by a flange 312. The reactor 300 extends longitudinally about an axis 20A-20A. A catalyst bed 340 may extend a suitable height within an internal space defined by the reactor shell 302.

The reactor 300 further defines a thermocouple insertion tube 326 extending about or substantially parallel or aligned with the longitudinal axis 20A-20A and through the catalyst bed 340. The thermocouple insertion tube 326 may be integrated with or independent of a tube bundle as described above. The thermocouple insertion tube 326 is configured to receive a temperature measurement device 310, which likewise extends about the longitudinal axis 20A-20A. The temperature measurement device 310 may be a multi-element thermocouple. The multi-element thermocouple is configured to obtain a measurement of a temperature at a plurality of locations along the reactor 300.

As seen in FIG. 20, the temperature measurement device 310 may comprise eight measurement locations 382A, 382B, 382C, 382D, 382E, 382F, 382G, 382H along the length of the reactor 300 and extends to a terminus 327. The temperature measurement device 310 may have a total length 3301. The locations 382A, 382B, 382C, 382D, 382E, 382F, 382G, 382H may be distanced by, respectively, distances 330A, 330B, 330C, 330D, 330E, 330F, 330G. The distances 330A, 330B, 330C, 330D, 330E, 330F, 330G may be a same distance such that the measurement locations are evenly spaced along the reactor 300, or may be different distances depending on the needs of a particular process.

The thermocouple insertion tube 326 may be suitably configured to allow the temperature measurement device 310 to obtain readings at the locations 382A, 382B, 382C, 382D, 382E, 382F, 382G, 382H, such as by defining apertures in the thermocouple insertion tube 326 at or proximate the locations 382A, 382B, 382C, 382D, 382E, 382F, 382G, 382H to allow the temperature measurement device 310 to gauge the temperature of the reactor interior. While a temperature measurement device has been described, it will be appreciated that the disclosure extends to other types of sensors and is not limited to a multi-element thermocouple. In embodiments, different sensors may be arranged at different locations as necessary.

The temperature measurement device 310, the reactor 300, and the thermocouple insertion tube 326 advantageously facilitate improved process control by providing granular reactor conditions data at multiple locations within a reactor while simultaneously minimizing the risk of leakage, particularly for high pressure and/or high temperature service and/or for reactions involving hydrogen or catalysts that are sensitive to oxygen, by reducing the number of thermocouple joints. The configuration of the temperature measurement device 310, the reactor 300, and the thermocouple insertion tube 326 further improves the scalability of a reactor design, as the arrangement of the thermocouple insertion tube 326 and the temperature measurement device 310 allows for an accurate reading of internal reactor conditions regardless of the size of the reactor, mitigating the difficulty of monitoring reactors in which thermowells are arranged radially from a sidewall surface of the reactor and, for larger reactors, disproportionately measure conditions near the shell rather than near the center of the reactor.

Figure 2:
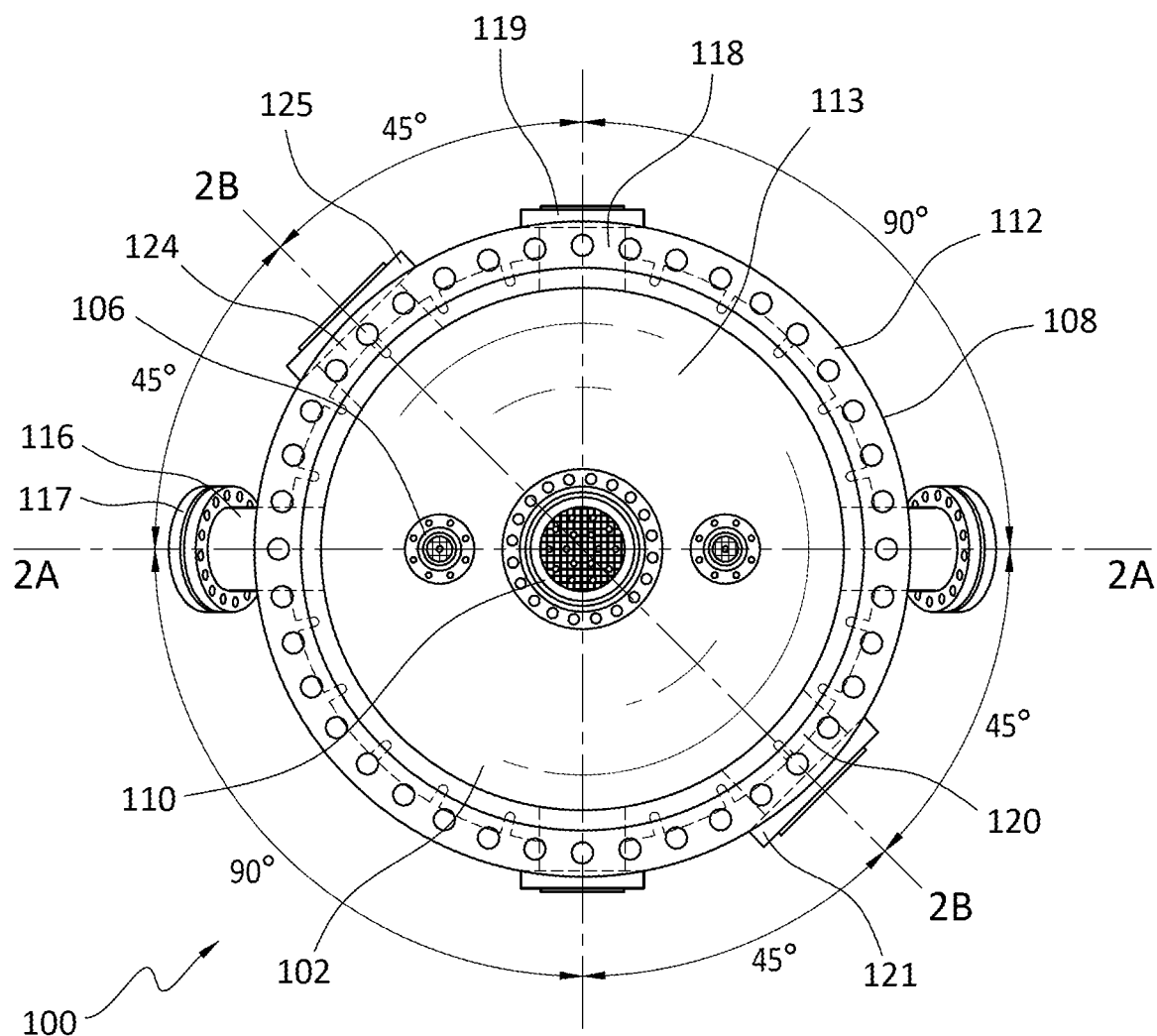
FIG. 2 is a plan view of the reactor according to the embodiment of FIG. 1A.

Additionally, as seen in at least FIGS. 2 and 7, a reactor may comprise a plurality of temperature measurement devices. The temperature measurement devices may be arranged in any suitable configuration relative to the reactor shell and to each other. In the embodiment of FIGS. 2 and 7, for example, the temperature measurement devices may be offset from a central longitudinal axis of the reactor by a same distance and arranged opposite each other. The distance between the temperature measurement devices may be configured to minimize interference with or disturbances in the heat distribution within the reactor, particularly the catalyst bed. The distance may be selected to be above a minimum threshold at which a hotspot would develop between or proximate the temperature measurement devices due to the resulting disruption to reactant and product flow and accordingly heat distribution. Arranging the temperature measurement devices above the minimum threshold thereby avoids performance disruptions of the reactor and improves accuracy of the measurement.

The temperature measurement devices may serve different purposes and/or may be complementary to each other. In the embodiment of FIGS. 2 and 7, the temperature measurement devices are multi-element thermocouples as described regarding FIG. 20. One of the multi-element thermocouples may be connected to a process control system, while a second one of the multi-element thermocouples may be connected to a safety instrument system.

Providing a plurality of the multi-element thermocouples advantageously confirms the measurement of temperature at a particular location, i.e. elevation, within the reactor. Any difference between the signals obtained from the multi-element thermocouples may be used to determine, for example, the development of a hot spot at a particular elevation, allowing an operator to make adjustments as necessary. It will be appreciated that any suitable number of thermocouples in any suitable configuration may be used.

An embodiment of the reactor comprises a plurality of feed tubes extending longitudinally through the reactor and a catalyst bed. A tube bundle may define thermocouple insertion tubes extending parallel to the feed tubes and configured to receive a temperature measurement device such as a multi-element thermocouple therethrough. The thermocouple insertion tubes may be configured to extend at different distances from a center of the reactor.

The distances may be configured to allow for measurement of a temperature distribution at different distances from the center. In particular, this may help to validate a design of the reactor at a particular scale, further enhancing the scalability of the reactor of embodiments of the present disclosure. This further enhances the process control of the reactor, with improved granularity of temperature measurement and the ability to tailor the associated responses using the process control system. In embodiments, the radial configuration of the thermocouple insertion tubes may be determined so as to coincide with predicted hotspots.

This allows an operator to quickly and accurately determine when a hotspot has formed and to respond accordingly, thereby preventing runaway reactions. The configuration of the thermocouple insertion tubes may further be determined relative to the tube bundle so as to accommodate the size of the reactor shell. In smaller reactors, for example, fewer thermocouple insertion tubes may be utilized, whereas the number of thermocouple insertion tubes, and the complexity of the configuration of the same, may increase in larger reactors.

By providing a reactor according to the disclosed embodiments, the problems of existing reactors being difficult to access when maintenance is needed, and reactors being difficult to scale based on the throughput needs of a facility, are addressed. The reactor embodiments of the present disclosure advantageously provide a reactor that comprises robust yet flexible reactor internals that are configured to be modularly arranged based on the throughput needs of a facility design, easily accessible for maintenance and catalyst loading, facilitate improved, even distribution of catalyst, reactants, and heat, and/or provide robust structural support during construction, transportation, installation, and operation.

While the reactor has been illustrated and described in detail in the drawings and foregoing description, the same is to be considered as illustrative and not restrictive in character, it being understood that only the preferred embodiments have been shown and described and that all changes, equivalents, and modifications that come within the spirit of the embodiments defined by following claims are desired to be protected.

Accordingly, features of the disclosed embodiments may be combined or arranged for achieving particular advantages as would be understood from the disclosure by one of ordinary skill in the art. Similarly, features of the disclosed embodiments may provide independent benefits applicable to other examples not detailed herein. In particular, any feature from one disclosed embodiment may be employed in another disclosed embodiment.

It is to be understood that not necessarily all objects or advantages may be achieved under any embodiment of the disclosure. Those skilled in the art will recognize that the reactor may be embodied or carried out in a manner that achieves or optimizes one advantage or group of advantages as taught without achieving other objects or advantages as taught or suggested.

The skilled artisan will recognize the interchangeability of various disclosed features. Besides the variations described, other known equivalents for each feature can be mixed and matched by one of ordinary skill in this art to make or use a reactor under principles of the present disclosure. It will be understood by the skilled artisan that the features described may be adapted to other types of reactors, reaction suites, chemical species, and processes. Hence this disclosure and the embodiments and variations thereof are not limited to methanol synthesis processes or to shell-and-tube reactors, but can be utilized in any chemical process.

Although this disclosure describes certain exemplary embodiments and examples of a reactor, it therefore will be understood by those skilled in the art that the present disclosure extends beyond the specifically disclosed embodiments to other alternative embodiments and/or uses of the disclosure and obvious modifications and equivalents thereof. It is intended that the present disclosure should not be limited by the particular disclosed embodiments described above.

In addition, unless otherwise indicated, numbers expressing quantities, constituents, distances, or other measurements used in the specification and claims are to be understood as optionally being modified by the term "about" or its synonyms. When the terms "about," "approximately," "substantially," or the like are used in conjunction with a stated amount, value, or condition, it may be taken to mean an amount, value or condition that deviates by less than 20%, less than 10%, less than 5%, less than 1%, less than 0.1%, or less than 0.01% of the stated amount, value, or condition. As used herein, the term "between" includes any referenced endpoints. For example, "between 2 and 10" includes both 2 and 10.

The invention claimed is:

1. A reactor comprising:
a shell defining an internal space configured to receive a catalyst;
at least one inlet nozzle; and
a tube bundle comprising a plurality of tubes arranged in concentric bands about a longitudinal axis of the reactor;
wherein the reactor further comprises at least one tube support plate, wherein the at least one tube support plate comprises at least one circumferential band, wherein the at least one circumferential band comprises at least one bracket configured to extend about a portion of a tube of the tube bundle.

2. The reactor of claim 1, further comprising at least one of a catalyst support plate, a gas inlet plate, or a top plate.

3. The reactor of claim 1, wherein the catalyst is a solid catalyst that comprises balls of a first diameter.

4. The reactor of claim 3, wherein the solid catalyst further comprises balls of a second diameter.

5. The reactor of claim 4, wherein the reactor further comprises a catalyst support plate, wherein the catalyst balls of the first diameter and the catalyst balls of the second diameter are arranged in discrete, respective layers proximate the catalyst support plate.

6. The reactor of claim 1, wherein the shell is configured to receive at least one solid catalyst, wherein the solid catalyst comprises a shape defining at least one of pellets, rings, tablets, or spheres.

7. The reactor of claim 1, wherein the reactor further comprises a catalyst support plate, wherein the catalyst support plate is configured to support a height of the solid catalyst.

8. The reactor of claim 1, wherein the reactor further comprises a catalyst support plate, wherein the catalyst support plate defines one or more apertures.

9. The reactor of claim 8, wherein the one or more apertures comprise a plurality of apertures of a first size and a plurality of apertures of a second size, the apertures extending through at least part of a thickness of the catalyst support plate.

10. The reactor of claim 9, wherein the first size corresponds to a circumference of at least one tube of the tube bundle, and the second size is smaller than the first size.

11. The reactor of claim 10, wherein the apertures of the first size are defined through the catalyst support plate according to an arrangement of the plurality of tubes of the tube bundle.

12. The reactor of claim 1, wherein the reactor further comprises a gas inlet plate, wherein the gas inlet plate comprises a plurality of apertures defined through a thickness of the gas inlet plate, wherein the plurality of apertures are circular apertures defined through the gas inlet plate according to the arrangement of the plurality of tubes of the tube bundle.

13. The reactor of claim 12, wherein the gas inlet plate further comprises a second plurality of apertures defined through the thickness of the gas inlet plate, the second plurality of apertures comprising a different size and/or shape than the plurality of circular apertures.

14. The reactor of claim 1, wherein the at least one tube support plate defines a plurality of concentric circumferential bands.

15. The reactor of claim 14, wherein the at least one tube support plate defines at least one radial strut connected to at least one of the plurality of circumferential bands.

16. The reactor of claim 14, wherein an innermost circumferential band of the at least one tube support plate comprises a given number of brackets configured respectively to correspond to a concentric band ring of the same given number of innermost tubes of the tube bundle, and a second circumferential band of the at least one tube support plate comprises an equal or greater number of brackets as compared to the innermost circumferential band, configured respectively to correspond to a corresponding number of tubes in a second concentric band ring of the tube bundle.

17. The reactor of claim 16, wherein one of the circumferential bands of the at least one tube support plate further comprises brackets corresponding to at least one thermocouple insertion tube, wherein the at least one thermocouple insertion tube is configured to receive a temperature measurement device, the temperature measurement device being configured to obtain a temperature at a plurality of longitudinal locations within the reactor.

18. A methanol synthesis reactor comprising:
  a shell defining an internal space configured to receive a solid catalyst;
  a tube bundle comprising a plurality of tubes, wherein the tubes are arranged in concentric bands about a longitudinal axis of the reactor;
  at least one inlet nozzle;
  an outlet nozzle, the outlet nozzle being located proximate a bottom portion of the shell;
  a catalyst support plate, wherein the outlet nozzle is arranged below the catalyst support plate;
  a plurality of tube support plates, wherein each tube support plate comprises a plurality of circumferential bands, wherein each circumferential band comprises at least one bracket configured to extend about a tube of the tube bundle;
  wherein each tube support plate defines a plurality of radial struts, each radial strut being connected between the circumferential bands of the tube support plate;
  wherein each radial strut is removably secured to at least one of the circumferential bands of each tube support plate; and
  a gas inlet plate, wherein the gas inlet plate is arranged proximate the inlet nozzle, with the inlet nozzle arranged below the gas inlet plate.

19. The reactor of claim 18, wherein the tube bundle is configured to facilitate a greater degree of heat transfer proximate a bottom portion of the reactor relative to a top portion of the reactor.

20. A reactor comprising:
  a shell defining an internal space configured to receive a catalyst;
  at least one inlet nozzle; and
  a tube bundle comprising a plurality of tubes arranged in concentric bands about a longitudinal axis of the reactor;
  wherein the reactor further comprises a gas inlet plate, wherein the gas inlet plate comprises a plurality of apertures defined through a thickness of the gas inlet plate, wherein the plurality of apertures are circular apertures defined through the gas inlet plate according to the arrangement of the plurality of tubes of the tube bundle;
  wherein the gas inlet plate further comprises a second plurality of apertures defined through the thickness of the gas inlet plate, the second plurality of apertures comprising a different size and/or shape than the plurality of circular apertures.

* * * * *